United States Patent
Ruminski et al.

(10) Patent No.: US 8,716,226 B2
(45) Date of Patent: May 6, 2014

(54) 3,5 PHENYL-SUBSTITUTED BETA AMINO ACID DERIVATIVES AS INTEGRIN ANTAGONISTS

(71) Applicant: Saint Louis University, St. Louis, MO (US)

(72) Inventors: Peter Ruminski, Wildwood, MO (US); David Griggs, Ballwin, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 13/944,319

(22) Filed: Jul. 17, 2013

(65) Prior Publication Data

US 2014/0051715 A1 Feb. 20, 2014

Related U.S. Application Data

(60) Provisional application No. 61/673,069, filed on Jul. 18, 2012.

(51) Int. Cl.
*A61K 38/36* (2006.01)

(52) U.S. Cl.
USPC ...................................................... 514/13.8

(58) Field of Classification Search
None
See application file for complete search history.

(56) References Cited

U.S. PATENT DOCUMENTS

| | | | |
|---|---|---|---|
| 5,602,155 A | 2/1997 | Ruminski | |
| 5,639,765 A | 6/1997 | Ruminski | |
| 5,681,820 A | 10/1997 | Ruminski | |
| 5,773,646 A | 6/1998 | Chandrakumar et al. | |
| 5,798,370 A | 8/1998 | Ruminski | |
| 5,840,961 A | 11/1998 | Behling et al. | |
| 5,852,210 A | 12/1998 | Chen et al. | |
| 6,013,651 A | 1/2000 | Rogers et al. | |
| 6,028,223 A | 2/2000 | Ruminski et al. | |
| 6,372,719 B1 | 4/2002 | Cunningham et al. | |
| 6,414,180 B1 | 7/2002 | Colson et al. | |
| 6,689,787 B1 | 2/2004 | McKearn et al. | |
| 6,933,304 B2 | 8/2005 | Nagarajan et al. | |
| 7,119,098 B2 | 10/2006 | Nagarajan et al. | |

FOREIGN PATENT DOCUMENTS

| EP | 1667668 | 7/2008 |
|---|---|---|
| WO | WO 96/23771 | 8/1996 |
| WO | WO 97/08145 | 3/1997 |
| WO | WO 97/36859 | 10/1997 |
| WO | WO 97/36860 | 10/1997 |
| WO | WO 97/36862 | 10/1997 |
| WO | WO 99/44994 | 9/1999 |
| WO | WO 99/44996 | 9/1999 |
| WO | WO 99/52896 | 10/1999 |
| WO | WO 00/51686 | 9/2000 |
| WO | WO 2004/060376 | 7/2004 |
| WO | WO 2008/018827 | 2/2008 |
| WO | WO 2010/010184 | 1/2010 |
| WO | WO 2010/104933 | 9/2010 |
| WO | WO 2011/025927 | 3/2011 |
| WO | WO 2012/027322 | 3/2012 |

OTHER PUBLICATIONS

Abdollahi et al., "Inhibition of alpha(v)beta3 integrin survival signaling enhances antiangiogenic and antitumor effects of radiotherapy," *Clin. Cancer Res.*, 11:6270-6279, 2005.
Adachi et al., "Significance of integrin alpha5 gene expression as a prognostic factor in node-negative non-small cell lung cancer," *Clin. Cancer Res.*, 6(1):96-101, 2000.
Asano et al., "Increased expression of integrin alpha(v)beta3 contributes to the establishment of autocrine TGF-beta signaling in scleroderma fibroblasts," *J. Immunol.*, 175(11):7708-7718, 2005.
Avraamides et al., "Integrins in angiogenesis and lymphangiogenesis," *Nat. Rev. Cancer*, 8(8):604-617, 2008.
Awasthi et al., "Practical enantioselective synthesis of β-substituted-β-amino esters," *J. Org. Chem.*, 70:5387-5397, 2005.
Babadzhanova et al., "Convenient syntheses of 1,1,1,3,3,3-hexafluoro-2- organyl-propan-2-ols and the corresponding trimethylsilyl ethers," *Tetrahedron*, 61(7):1813-1819, 2005.
Bax et al., "Cell adhesion to fibrillin-1 molecules and microfibrils is mediated by alpha 5 beta 1 and alpha v beta 3 integrins," *J. Biol. Chem.*, 278(36):34605-34616, 2003.
Becker et al., "An expedient synthesis of 3-amino-5-hydroxy-benzoic acid and its n-alkyl analogues," *Tetrahedron*, 39:4189-4192, 1983.

(Continued)

*Primary Examiner* — Thomas Heard
(74) *Attorney, Agent, or Firm* — Parker Highlander PLLC

(57) ABSTRACT

Disclosed herein are novel pharmaceutical agents which are useful as integrin receptor antagonists that mediate the pathologic processes of angiogenesis and fibrosis and as such are useful in pharmaceutical compositions and in methods for treating conditions mediated by these integrins by inhibiting or antagonizing these integrins. The novel pharmaceutical agents include those of the formula:

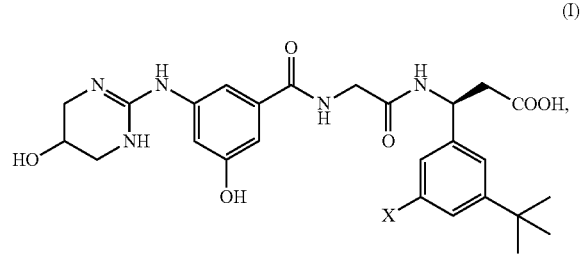

(I)

wherein X is bromo or iodo, or pharmaceutically acceptable salts thereof. Also provided are pharmaceutical compositions, kits and articles of manufacture comprising such pharmaceutical agents. Methods and intermediates useful for making the pharmaceutical agents and methods of using the pharmaceutical agents are also provided.

4 Claims, No Drawings

(56) References Cited

OTHER PUBLICATIONS

Bhaskar et al., "A function blocking anti-mouse integrin alpha5beta1 antibody inhibits angiogenesis and impedes tumor growth in vivo," *J. Transl. Med.*, 5:61, 2007.

Blase et al., "The capacity of human malignant B-lymphocytes to disseminate in SCID mice is correlated with functional expression of the fibronectin receptor alpha 5 beta 1 (CD49e/CD29)," *Int. J. Cancer*, 60(6):860-866, 1995.

Carron et al., "A peptidomimetic antagonist of the integrin avb3 inhibits Leydig cell tumor growth and the development of hypercalcemia of malignancy," *Cancer Res.*, 58:1930-1935, 1998.

Carron et al., "Peptidomimetic antagonists of avb3 inhibit bone resorption by inhibiting osteoclast bone resorptive activity, not osteoclast adhesion to b one," *J. Endocrinol.*, 165:587-598, 2000.

Chai et al., "αv and β1 integrins regulate dynamic compression-induced proteoglycan synthesis in 3D gel culture by distinct complementary pathways," *Osteoarthritis and Cartilage*, 18:249-256, 2009.

Clark, et al., "Pilot Plant Preparation of an αvβ3 Integrin Antagonist. Part 1. Process Research and Development of a (S)-β-Amino Acid Ester Intermediate: Synthesis via a Scalable, Diastereoselective Imino-Reformatsky Reaction," *Organic Process Research & Development*, 8:51-61, 2004.

Clark, et al., "Pilot-Plant Preparation of an αv133 Integrin Antagonist. Part 2. Synthesis of N-[2-(5-Hydroxy-4,6-tetrahydropyrimidine)]-3-amino-5-hydroxybenzoic Acid," *Organic Process Research & Development*, 8:571-575, 2004.

Collo, "Endothelial cell integrin alpha5beta1 expression is modulated by cytokines and during migration in vitro," *J. Cell Sci.*, 112(Pt 4):569-578, 1999.

Cue et al., "A nonpeptide integrin antagonist can inhibit epithelial cell ingestion of *Streptococcus pyogenes* by blocking formation of integrin alpha 5beta 1-fibronectin-M1 protein complexes," *Proc Natl Acad Sci USA*, 97(6):2858-2863, 2000.

Danen et al., "Emergence of alpha 5 beta 1 fibronectin- and alpha v beta 3 vitronectin-receptor expression in melanocytic tumour progression," *Histopathology*, 24(3):249-256, 1994.

Database Registry, Chemical Abstracts Service, Database accession No. 773126-23-1, retrieved from STN, 2004.

Database Registry, Chemical Abstracts Service, Database accession No. 682803-43-6, retrieved from STN, 2011.

Database Registry, Chemical Abstracts Service, Database accession No. 1270085-65-8, retrieved from STN, 2011.

Duggan et al., "Ligands to the integrin receptor alphavbeta3," *Expert Opinion on Therapeutic Patents*, 10(9):1367-1383, 2000.

Edward, "Integrins and other adhesion molecules involved in melanocytic tumor progression." *Curr. Opin. Oncol.*, 7(2):185-191, 1995.

Engleman et al., "A peptidomimetic antagonist of the avb3 integrin inhibits bone resorption in vitro and prevents osteoporosis in vivo," *J. Clin. Invest.*, 99:2284-2292, 1997.

Faulconbridge et al., "Preparation of enantiomerically enriched aromatic β-amino acids via enzymatic resolution," *Tetrahedron Lett.*, 41:2679-2681, 2000.

Ferrari et al., "VEGF, a prosurvival factor, acts in concert with TGF-beta1 to induce endothelial cell apoptosis," *Proc Natl Acad Sci USA*, 103(46):17260-17265, 2006.

Gao and Brigstock, "A novel integrin alpha5beta1 binding domain in module 4 of connective tissue growth factor (CCN2/CTGF) promotes adhesion and migration of activated pancreatic stellate cells." *Gut*, 55:856-862, 2006.

Gisch et al., "Enzymatically Activated cycloSal-d4T-monophosphates: The Third Generation of cycloSal-Pronucleotides," *J. Med. Chem.*, 50:1658-1667, 2007.

Gisch et al., "Studies on Enzyme-Cleavable Dialkoxymethyl-cycloSaligenyl-2',3'-dideoxy-2',3'-didehydrothymidine Monophosphates," *J. Med. Chem.*, 51:6752-6760, 2008.

Goodman et al., "Nanomolar small molecule inhibitors for alphav(beta)6, alphav(beta)5, and alphav(beta)3 integrins," *J Med Chem.*, 45(5):1045-1051, 2002.

Griggs et al., "Characteristics of cation binding to the I domains of LFA-1 and MAC-1," *J. Biol. Chem.*, 273:22113-22119, 1998.

Griggs et al., "Promoter elements determining weak expression of the GAL4 regulatory gene of *Saccharomyces cerevisiae*," *Mol. Cell. Biol.*, 13(8):4999-5009, 1993.

Griggs et al., "Regulated expression of the GAL4 activator gene in yeast provides a sensitive genetic switch for glucose repression," *Proc. Natl. Acad. Sci.*, 88:8597-8601, 1991.

Harms et al., "A small molecule antagonist of the αvβ3 integrin suppresses MDA-MB-435 skeletal metastasis," *Clin. Exp. Metastasis*, 21:119-128, 2004.

Heckman et al., "Probing integrin selectivity: rational design of highly active and selective ligands for the alpha5beta1 and alphavbeta3 integrin receptor," *Angew Chem Int Ed Engl.*, 46(19):3571-3574, 2007.

Heckman et al., "Rational design of highly active and selective ligands for the alpha5beta1 integrin receptor," *Chembiochem.*, 9(9):1397-1407, 2008.

Henderson et al., "Selective αv integrin deletion identifies a core, targetable molecular pathway that regulates fibrosis across solid organs," *Nature Medicine*, in press, 2013.

Herlt et al., "Synthesis of unlabeled and carboxyl-labelled 3-amino-5- hydroxybenzoic acid," *Austr. J. Chem.*, 34(6):1319-1324, 1981.

Hippenmeyer et al., "Adenovirus inhibition by peptidomimetic integrin antagonists," *Antiviral Res.*, 55:169-178, 2002.

Horan et al., "Partial inhibition of integrin alpha(v)beta6 prevents pulmonary fibrosis without exacerbating inflammation." *Am. J. Respir. Crit. Care Med.*, 177(1):56-65, 2008.

Huang, et al., "Direct Trifluoromethylation of Nitriles Promoted by Tetrabutylammonium Bifluoride," *Synlett*, 15:2518-2520, 2009.

Jørgensen, et al., "Efficient Synthesis of α-Aryl Esters by Room-Temperature Palladium-Catalyzed Coupling of Aryl Halides with Ester Enolates," *J. Am. Chem. Soc.*, 124(42):12557-12565, 2002.

Kapp et al., "Integrin modulators: a patent review." *Institute for Advanced Study and Center for Integrated Protein Science.* Oct. 2013: 23(10): 1273-95.

Kim et al., "Regulation of angiogenesis in vivo by ligation of integrin alpha5beta1 with the central cell-binding domain of fibronectin." *Am. J. Pathol.*, 156(4):1345-1362, 2000.

Kurahashi et al., "One-Electron Oxidation of Electronically Diverse Manganese(III) and Nickel(II) Salen Complexes: Transition from Localized to Delocalized Mixed-Valence Ligand Radicals," *J. Am. Chem. Soc.*, 133(21):8307-8316, 2011.

Landis et al., "Kinetic Resolution of β-Amino Esters by Acylation Using Immobilized Penicillin Amidohydrolase," *Organic Process Research & Development*, 6:539-546, 2002.

Li et al., "Integrin alpha5beta1 mediates attachment, migration, and proliferation in human retinal pigment epithelium: relevance for proliferative retinal disease." *Invest. Ophthalmol. Vis. Sci.*, 50(12):5988-5996, 2009.

Livant et al., "The PHSRN sequence induces extracellular matrix invasion and accelerates wound healing in obese diabetic mice." *J. Clin. Invest.*, 105(11):1537-1545, 2000.

Lobert et al., "Ubiquitination of alpha 5 beta 1 integrin controls fibroblast migration through lysosomal degradation of fibronectin-integrin complexes." *Dev. Cell*, 19(1):148-159, 2010.

Malfait et al., "Proprotein convertase activation of accrecanases in cartilage in situ," *Arch. Biochem. Biophys.*, 478:43-51, 2008.

Melton et al., "Expression of αvβ8 integrin on dendritic cells regulates Th17 cell development and experimental autoimmune encephalomyelitis in mice." *J. Clin. Invest.*, 120(12):4436-4444, 2010.

Millard et al., "Integrin targeted therapeutics." *Theranostics*, 1:154-88, 2011.

Mu et al., "The integrin alpha(v)beta8 mediates epithelial homeostasis through MT1-MMP-dependent activation of TGF-beta1." *Cell Biol.*, 157(3):493-507, 2002.

Munger et al., "Interactions between growth factors and integrins: latent forms of transforming growth factor-beta are ligands for the integrin alphavbeta1." *Mol. Biol. Cell*, 9:2627-2638, 1998.

Munger et al., The integrin alpha v beta 6 binds and activates latent TGF beta 1: a mechanism for regulating pulmonary inflammation and fibrosis. *Cell.*, 96(3):319-328, 1999.

(56) References Cited

OTHER PUBLICATIONS

Nagarajan et al., "Discovery of diphenylmethanepropionic and dihydrostilbeneacetic acids as antagonists of the integrin αvβ3," *Chem. Biol. Drug Des.*, 67:177-181, 2006.

Nagarajan et al., "R-isomers of Arg-Gly-Asp (RGD) mimics as potent alphavbeta3 inhibitors," *Bioorganic & Medicinal Chemistry*, 15(11):3783-3800, 2007.

Nandrot et al., "Novel role for alphavbeta5-integrin in retinal adhesion and its diurnal peak," *Am J Physiol Cell Physiol*, 290(4):C1256-C1262, 2006.

Nishimura, "Integrin-mediated transforming growth factor-beta activation, a potential therapeutic target in fibrogenic disorders." *Am. J. Pathol.*, 175(4):1362-1370, 2009.

Nomura et al., "Stereoselective Ring-Opening Polymerization of a Racemic Lactide by Using Achiral Salen—and Homosalen—Aluminum Complexes," *Chemistry—A Europ. J.*, 13(16):4433-4451, 2007.

PCT International Search Report issued in International Application No.PCT/US2013/050917, mailed Sep. 23, 2013.

Perdih, "Small molecule antagonists of integrin receptors." *Curr. Med.Chem.*, 17(22):2371-2392, 2010.

Popov et al., "Integrin alphavbeta6 is a marker of the progression of biliary and portal liver fibrosis and a novel target for antifibrotic therapies." *J. Hepatol.*, 48(3):453-464, 2008.

Rico, "Synthesis of novel β-amino acid precursors: β-aminohydrocoumarins as unusual aspartic acid mimetics used in fibrinogen receptor antagonists,"*Tett. Let.*, 35:6599-6602, 1994.

Schmidt et al., "Characterization of spontaneous metastasis in an aggressive breast carcinoma model using flow cytometry," *Clin. Exp. Metastasis*, 17:537-544, 1999.

Scotton et al., "Increased local expression of coagulation factor X contributes to the fibrotic response in human and murine lung injury," *J Clin Invest.*, 119(9):2550-2563, 2009.

Shannon et al., "Anti-metastatic properties of RGD-peptidomimetic agents S137 and S247," *Clin. Exp. Metastasis*, 21:129-138, 2004.

Song et al., "Aggrecan degradation in human articular cartilage explants is mediated by both ADAMTS-4 and ADAMTS-5," *Arthritis Rheum.*, 56:575-585, 2007.

Stragies et al., "Design and synthesis of a new class of selective integrin alpha5beta1 antagonists," *J Med Chem.*, 50(16):3786-3794, 2007.

Suehiro et al., "Fibrinogen binds to integrin alpha(5)beta(1) via the carboxyl terminal RGD site of the Aalpha-chain" *J. Biochem.*, 128(4):705-710, 2000.

Tanaka and Shishido, "Synthesis of aromatic compounds containing a 1,1-dialkyl-2-trifluoromethyl group, a bioisostere of the tert-alkyl moiety," *Bioorg. Med. Chem. Lett.*, 17(22):6079-6085, 2007.

Wan, et al., "Synthesis of Potent and Orally Efficacious 11β-Hydroxysteroid Dehydrogenase Type 1 Inhibitor HSD-016," *J. Org. Chem.*, 76(17):7048-7055, 2011.

Wipff et al., "Myofibroblast contraction activates latent TGF-beta1 from the extracellular matrix." *J. Cell Biol.*, 179(6):1311-1323, 2007.

Wong et al., "av integrins mediate adhesion and migration of breast carcinoma cell lines," *Clin. Exp. Metastasis*, 16:50-61, 1998.

Wu, et al., "Mild Palladium-Catalyzed Selective Monoarylation of Nitriles," *J. Am. Chem. Soc.*, 127(45):15824-15832, 2005.

Yang et al., "Embryonic mesodermal defects in alpha 5 integrin-deficient mice." Development, 119(4):1093-1105, 1993.

Yoshimura and Muto, "TGF-βfunction in immune suppression," *Curr Top Microbiol Immunol.*, 350:127-147, 2011.

Zack et al., "ADAM-8 isolated from human osteoarthritic chondrocytes is capable of cleaving fibronectin at Ala271," *Arthritis Rheum.*, 60:2704-2713, 2009.

Zahn et al., "Assessment of the integrin alpha5beta1 antagonist JSM6427 in proliferative vitreoretinopathy using in vitro assays and a rabbit model of retinal detachment." *Invest. Ophthalmol. Vis. Sci.*, 51(2):1028-1035, 2010.

Zahn et al., "Preclinical evaluation of the novel small-molecule integrin alpha5beta1 inhibitor JSM6427 in monkey and rabbit models of choroidal neovascularization." *Arch. Ophthalmol.*, 127(10):1329-1335, 2009.

3,5 PHENYL-SUBSTITUTED BETA AMINO ACID DERIVATIVES AS INTEGRIN ANTAGONISTS

PRIORITY CLAIM

This application claims the Benefit of U.S. Provisional Patent Application No. 61/673,069, filed Jul. 18, 2012, the entirety of which is incorporated herein by reference.

BACKGROUND OF THE INVENTION

I. Field of the Invention

The present invention relates to the fields of pharmaceuticals, medicine and cell biology. More specifically, it relates to pharmaceutical agents (compounds) which are useful as integrin receptor antagonists, with particularly exceptional biological activity as antagonists of a group of integrins that mediate the pathologic processes of angiogenesis and fibrosis. As such, these compounds are useful in pharmaceutical compositions and in methods for treating conditions mediated by such integrins by inhibiting or antagonizing these integrins.

II. Description of Related Art

Integrins are a family of integral cytoplasmic membrane proteins that mediate cell interactions with other cells and with the extracellular matrix. Approximately one third of the members of the integrin family directly bind to a specific amino acid motif, arginine-glycine-asparate (RGD), that is contained within the sequence of their cognate protein ligands. It has been established in the art that peptides containing the RGD sequence, and synthetic small molecule compounds that mimic the RGD sequence, are capable of binding to these integrin receptors with varying degrees of specificity, and thereby inhibit the binding to normal physiologic ligands (Millard et al., 2011.). The biological effects of treatment with such agents is dependent on intrinsic molecular properties, reflected in the structure, that determine to what degree a particular integrin, or combination of integrins, is inhibited in a body tissue over a period of time.

Many human diseases are characterized by either or both of two common contributing pathological mechanisms: angiogenesis and fibrosis. Different subsets of the RGD-binding integrins have predominant roles in driving these dual processes, so that simultaneous antagonism of angiogenesis and fibrosis requires agents capable of binding potently to several target integrins. This contrasts with agents designed specifically for binding to a single integrin which may be less effective in some applications due to their more restricted mechanism of action.

Integrins which have been shown to have a role in promoting angiogenesis include, $\alpha v \beta 3$, $\alpha v \beta 5$, and $\alpha 5\beta 1$. $\alpha v \beta 3$ and $\alpha v \beta 5$ were initially described as mediators of bFGF- and VEGF-induced angiogenesis, respectively, in corneal or choriallantoic models. More recently, data from studies using mice lacking these integrins also support an important functional role for $\alpha 5\beta 1$. The integrin $\alpha 5\beta 1$ (also known as VLA-5) is often referred to as the 'classic fibronectin receptor' reflecting its well characterized interaction with this extracellular matrix protein. Cells expressing $\alpha 5\beta 1$ bind to fibronectin in a region that incorporates the ninth and tenth type III fibronectin repeats, the latter of which contains the RGD motif critical for integrin binding. In addition to fibronectin, $\alpha 5\beta 1$ has been reported to interact with other RGD-containing extracellular matrix proteins including fibrinogen, denatured collagen, and fibrillin-1 (Bax et al., 2003; Perdih, 2010; Suchiro et al., 2000). These ligands are components of the provisional matrix that is laid down by cells as part of the wound healing response in tissues. Key components of this response are angiogenesis (new blood vessel formation) and fibrosis (scar formation) which are beneficial for healing of acute injuries, but can be deleterious in many disease contexts.

Antagonists of RGD-binding integrins should be useful for treatment of human diseases having angiogenesis or fibrosis as a principal part of their pathology. In particular, the important role of $\alpha 5\beta 1$ in angiogenesis is supported by numerous studies. For example, mice lacking this integrin exhibit embryonic lethality at day 10-11 with a phenotype that includes defects in both the embryonic and extraembryonic vasculature (Yang et al., 1993). Angiogenic cytokines such as bFGF, IL-8, TGF$\beta$, and TNF$\alpha$ upregulate $\alpha 5\beta 1$ expression on endothelial cells in vitro and in vivo, and immunohistochemistry shows coordinated increases in both $\alpha 5\beta 1$ and fibronectin staining in blood vessels from various types of human tumor biopsies and xenograft tumors in animals (Collo, 1999; Kim et al., 2000). Monoclonal antibodies that specifically inhibit $\alpha 5\beta 1$, and compounds that have been described as $\alpha 5\beta 1$ inhibitors, significantly reduce angiogenesis in a number of experimental models (Kim et al., 2000; Bhaskar et al., 2007; Livant et al., 2000; Zahn et al., 2009).

Because $\alpha 5\beta 1$ expression is not confined to the endothelium, it has other functional roles in addition to angiogenesis. It is expressed to varying degrees in many cell types including fibroblasts, hematopoietic and immune cells, smooth muscle cells, epithelial cells, and tumor cells. Expression on tumor cells has been implicated in the progression of tumor growth and metastasis (Adachi et al., 2000; Blasé et al., 1995; Danen et al., 1994; Edward, 1995). In human fibroblasts, $\alpha 5\beta 1$ promotes motility and survival (Lobert et al., 2010). In pancreatic stellate cells, it interacts with connective tissue growth factor to stimulate adhesion, migration, and fibrogenesis (Gao and Brigstock, 2006). It has been shown that pharmacologic antagonism of $\alpha 5\beta 1$ inhibits the attachment migration, and proliferation of human retinal epithelial cells in vitro, and reduces retinal cell proliferation and scarring when administered intravitreally to rabbits with retinal detachment (Li et al., 2009; Zahn et al., 2010).

Multiple RGD-binding integrins of the alpha v family have been implicated in promoting the biological activation of the latent pro-fibrotic cytokine TGF$\beta$. This is mediated by binding to the latency associated peptide (LAP), particularly by $\alpha v \beta 6$ and $\alpha v \beta 8$, but also by $\alpha v \beta 1$, $\alpha v \beta 3$, and $\alpha v \beta 5$. These integrin interactions are all critically dependent upon the amino acid sequence arg-gly-asp (RGD) contained in LAP. Indeed, mice containing a mutation in the RGD sequence are incapable of cytokine activation and phenocopy TGF$\beta$-null mice. It is anticipated that simultaneous inhibition of multiple integrins with the potential to activate TGF$\beta$ may have particular utility to prevent or treat a range of fibrotic conditions. In addition, such broad spectrum integrin antagonists may be particularly useful for simultaneous modulation of both angiogenesis and fibrosis.

SUMMARY OF THE INVENTION

The present disclosure provides novel integrin receptor antagonists, pharmaceutical compositions, and methods for their manufacture, and methods for their use.

In one aspect, there are provided compounds of the formula:

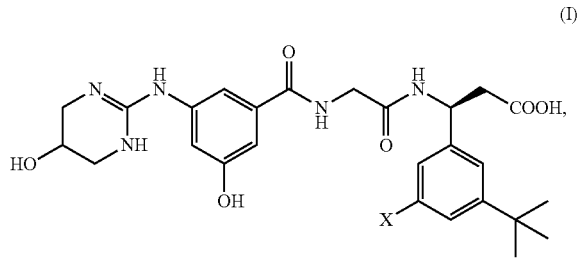

wherein X is bromo or iodo, or a pharmaceutically acceptable salt or tautomer thereof. In some embodiments, the compound is further defined as:

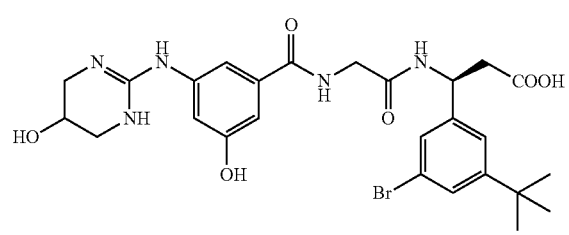 [SMILES: CC(C)(C)c1cc(Br)cc([C@H](CC(=O)O)NC(=O)CNC(=O)c2cc(O)cc(NC3=NCC(O)CN3)c2)c1]

or a pharmaceutically acceptable salt or tautomer thereof. In other embodiments, the compound is further defined as:

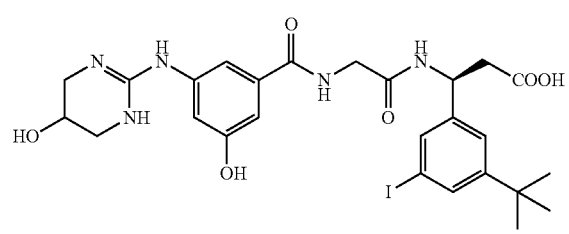 [SMILES: CC(C)(C)c1cc(I)cc([C@H](CC(=O)O)NC(=O)CNC(=O)c2cc(O)cc(NC3=NCC(O)CN3)c2)c1]

or a pharmaceutically acceptable salt or tautomer thereof.

In another aspect, the present invention provides a pharmaceutical composition comprising: a compound of the present invention and an excipient.

In yet another aspect, the present invention provides a method of treating and/or preventing a disease or a disorder in a patient in need thereof, comprising administering to the patient a compound of the present invention in an amount sufficient to treat and/or prevent the disease or disorder. In some embodiments, the disease or disorder is associated with angiogenesis. In other embodiments, the disease or disorder is associated with fibrosis. In other embodiments, the disease or disorder is associated with fibrosis and/or angiogenesis. In some embodiments, the disease or disorder is pulmonary, liver, renal, cardiac, and pancreatic fibrosis, scleroderma, scarring, retinopathy of prematurity, familial exudative vitreoretinopathy, proliferative vitreoretinopathies, macular degeneration, diabetic retinopathy, cancer, osteoporosis, autoimmune diseases, humoral hypercalcemia of malignancy, Paget's disease, periodontal disease, psoriasis, arthritis, restenosis, and infection. In some embodiments, the disease or disorder is pulmonary fibrosis. In other embodiments, the disease or disorder is liver fibrosis. In other embodiments, the disease or disorder is cardiac fibrosis. In other embodiments, the disease or disorder is renal fibrosis. In other embodiments, the disease or disorder is pancreatic fibrosis. In other embodiments, the disease or disorder is scleroderma. In other embodiments, the disease or disorder is scarring. In some embodiments, the scarring is dermal scarring. In other embodiments, the scarring is retinal scarring. In other embodiments, the scarring is corneal scarring. In other embodiments, the disease or disorder is retinopathy of prematurity. In other embodiments, the disease or disorder is familial exudative vitreoretinopathy. In other embodiments, the disease or disorder is proliferative vitreoretinopathies. In other embodiments, the disease or disorder is macular degeneration. In other embodiments, the disease or disorder is diabetic retinopathy. In other embodiments, the disease or disorder is cancer. In some embodiments, the cancer includes solid tumor growth or neoplasia. In other embodiments, the cancer includes tumor metathesis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma. In other embodiments, the disease or disorder is osteoporosis. In other embodiments, the disease or disorder is an autoimmune disease. In some embodiments, the autoimmune disorder is multiple sclerosis. In other embodiments, the disease or disorder is humoral hypercalcemia of malignancy. In other embodiments, the disease or disorder is Paget's disease. In other embodiments, the disease or disorder is periodontal disease. In other embodiments, the disease or disorder is psoriasis. In other embodiments, the disease or disorder is arthritis. In some embodiments, the arthritis is rheumatoid arthritis. In other embodiments, the disease or disorder is restenosis. In other embodiments, the disease or disorder is an infection. In some embodiments, the patient is a human, monkey, cow, horse, sheep, goat, dog, cat, mouse, rat, guinea pig, or transgenic species thereof. In other embodiments, the patient is a monkey, cow, horse, sheep, goat, dog, cat, mouse, rat, or guinea pig. In other embodiments, the patient is a human.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions with integrin receptor antagonists properties, methods for their manufacture, and methods for their use, including for the treatment and/or prevention of disease.

I. Definitions

When used in the context of a chemical group, "hydrogen" means —H; "hydroxy" means —OH; "oxo" means =O;

"halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "----" represents an optional bond, which if present is either single or double. The symbol "$\equiv\equiv\equiv$" represents a single bond or a double bond. Thus, for example, the structure

includes the structures

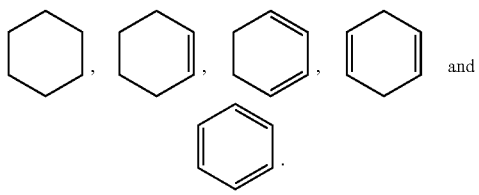

As will be understood by a person of skill in the art, no one such ring atom forms part of more than one double bond. The symbol "∿∿", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "▥▥▥" means a single bond where the group attached to the thick end of the wedge is "into the page". The symbol "∿∿" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

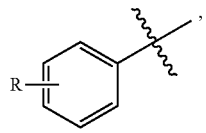

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

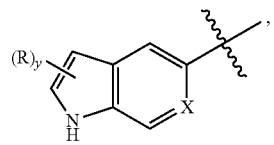

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

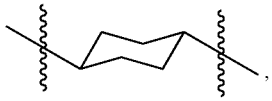 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

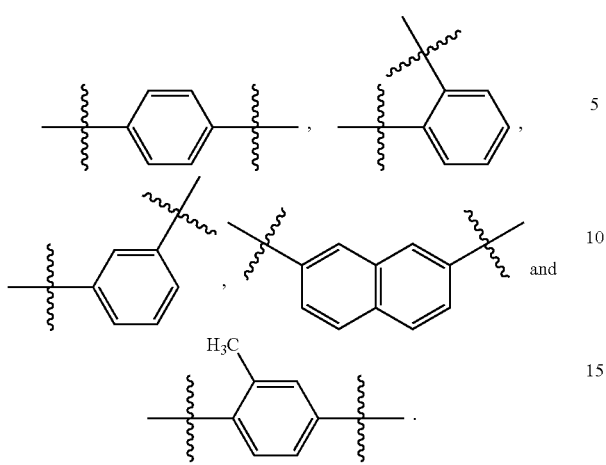

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

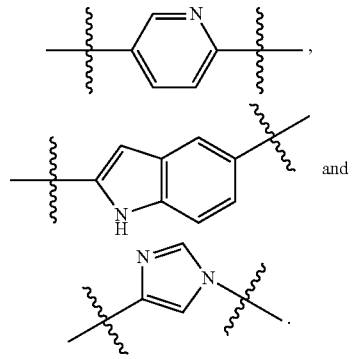

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃ (methoxy), —OCH₂CH₃ (ethoxy), —OCH₂CH₂CH₃, —OCH(CH₃)₂ (isopropoxy), —OCH(CH₂)₂, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl—, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. The term "alkyliminodiyl" refers to the divalent group —NH-alkanediyl—, —NH-alkanediyl—NH—, or -alkanediyl—NH-alkanediyl-. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups —NHC(O)OCH₃ and —NHC(O)NHCH₃ are non-limiting examples of substituted amido groups.

The terms "alkylsulfonyl" and "alkylsulfinyl" when used without the "substituted" modifier refers to the groups —S(O)₂R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC₅₀" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

Other abbreviations used herein are as follows: $^1$H-NMR is proton nuclear magnetic resonance, AcOH is acetic acid, Ar is argon, $CH_3CN$ is acetonitrile, CHN analysis is carbon/hydrogen/nitrogen elemental analysis, CHNCl analysis is carbon/hydrogen/nitrogen/chlorine elemental analysis, CHNS analysis is carbon/hydrogen/nitrogen/sulfur elemental analysis, DI water is deionized water, DIC is diisopropyl carbodiimide, DMA is N,N-dimethylacetamide, DMAP is 4-(N,N-dimethylamino)pyridine, DMF is N,N-dimethylformamide, EDCl is 1-(3-dimethylaminopropyl)-3-ethylcarbodiimide hydrochloride, EtOAc is ethyl acetate, EtOH is ethanol, FAB MS is fast atom bombardment mass spectroscopy, g is gram(s), HOBT is 1-hydroxybenzotriazole hydrate, HPLC is high performance liquid chromatography, IBCF is isobutyl-chloroformate, KSCN is potassium thiocyanate, L is liter, LiOH is lithium hydroxide, MEM is methoxyethoxymethyl, MEMCl is methoxyethoxymethyl chloride, MeOH is methanol, mg is milligram, $MgSO_4$ is magnesium sulfate, ml is milliliter, mL is milliliter, MS is mass spectroscopy, MTBE is methyl tert-butyl ether, $N_2$ is nitrogen, $NaHCO_3$ is sodium bicarbonate, NaOH is sodium hydroxide, $Na_2SO_4$ is sodium sulfate, NMM is N-methylmorpholine, NMP is N-methylpyrrolidinone, NMR is nuclear magnetic resonance, $P_2O_5$ is phosphorous pentoxide, PTSA is para-toluenesulfonic acid, RPHPLC is reverse phase high performance liquid chromatography, RT is room temperature, TFA is trifluoroacetic acid, THF is tetrahydrofuran, TMS is trimethylsilyl, and Δ is heating the reaction mixture.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds and Synthetic Methods

The compounds provided by the present disclosure may be made using the methods outlined below and further described in the Examples section. General synthetic sequences for preparing the compounds useful in the present invention are outlined in Schemes I-VII. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention. Starting materials and equipment employed were either commercially available or prepared by methods previously reported and readily duplicated by those skilled in the art.

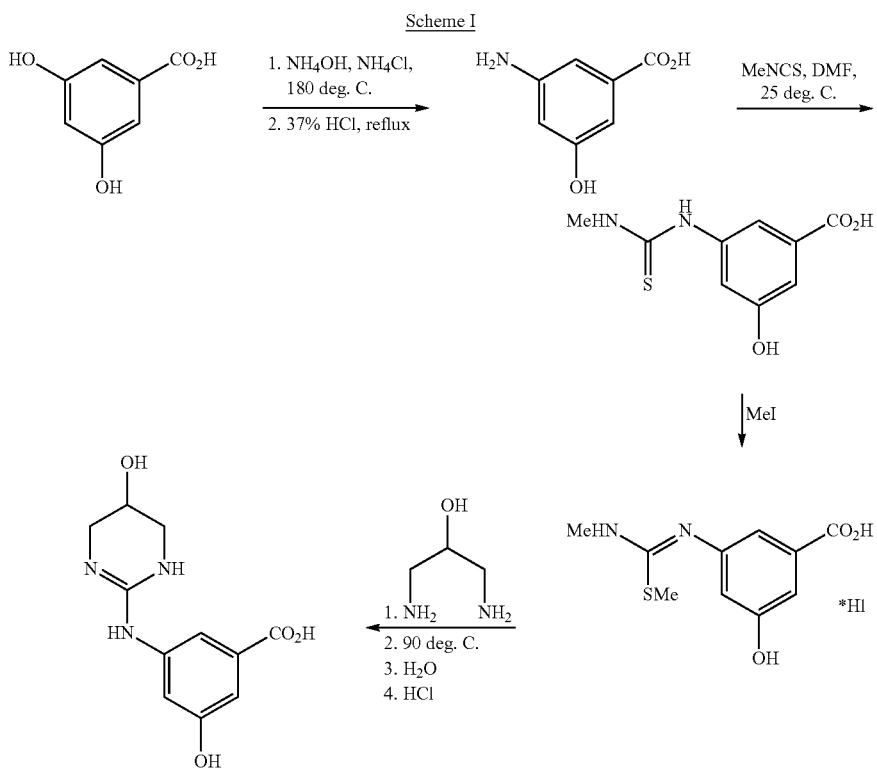

Scheme I

Scheme I illustrates methodology useful for preparing the tetrahydropyrimidinobenzoic acid portion of Formula I of the present invention which can then be coupled to a gly-β-amino acid ester, or to gly ester first, followed by (after ester hydrolysis) coupling to the appropriate β-amino acid ester. Briefly, in Scheme II, 3,5-dihydroxybenzoic acid is converted to 3-amino-5-hydroxy-benzoic acid using the procedure described in *Austr. J. Chem.* (1981) or Becker et al., (1983). The product is reacted with methyl isothiocyanate in DMF at room temperature (*Organic Process Research & Development*, 2004) to give 3-N'-methyl thiourea-5-hydroxybenzoic acid after normal work-up. This thiourea intermediate is converted to the S-methyl derivative by reaction with methyl iodide neat at below 40° C. 1,3-diamino-2-hydroxypropane is reacted with this resulting intermediate in hot DMA (or DMF). Upon cooling, a precipitate forms and the zwitterionic product is isolated by filtration. The HCl salt may be obtained by lyophilizing from dilute hydrochloric acid. Alternatively, the product may be isolated from the original reaction mixture by removing volatiles and concentrating. The resulting product is taken up in water and pH adjusted to about 5-7 where zwitterionic product precipitates and is isolated by filtration. The HCl salt may be obtained as previously stated or by simply dissolving in dilute hydrochloric acid and concentrating to a solid and drying.

Scheme II

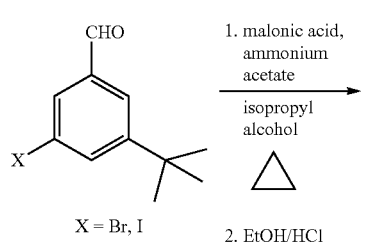

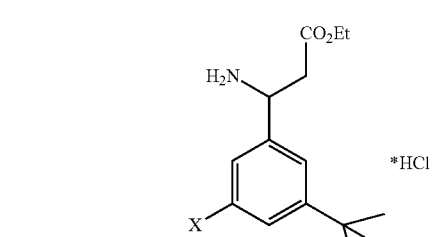

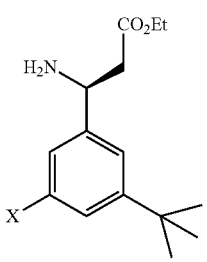 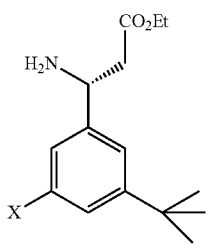

Scheme II illustrates a general methodology for the synthesis of the beta amino acid ester portion of Formula I of the present invention, starting from an appropriate benzaldehyde. This beta amino acid ester can then be coupled to Boc-glycine followed by (after removal of the Boc protecting group) coupling to the benzoic acid described in Scheme I, or to the benzoic acid that has been coupled to glycine. Briefly in Scheme II, to the appropriate benzaldehyde in isopropanol is added ammonium acetate followed by malonic acid. The reaction mixture is stirred at reflux, the resulting precipitate filtered and washed with hot isopropanol and dried to yield the desired racemic beta amino acid. The ethyl ester is synthesized by heating this acid in excess ethanol in the presence of excess HCl gas. These racemic beta amino acid esters can be resolved into the (R) and the preferred (S) enantiomers via chiral chromatographic separation, or via enzymatic resolution as described in Faulconbridge et al. (2000) or Landis et al. (2002).

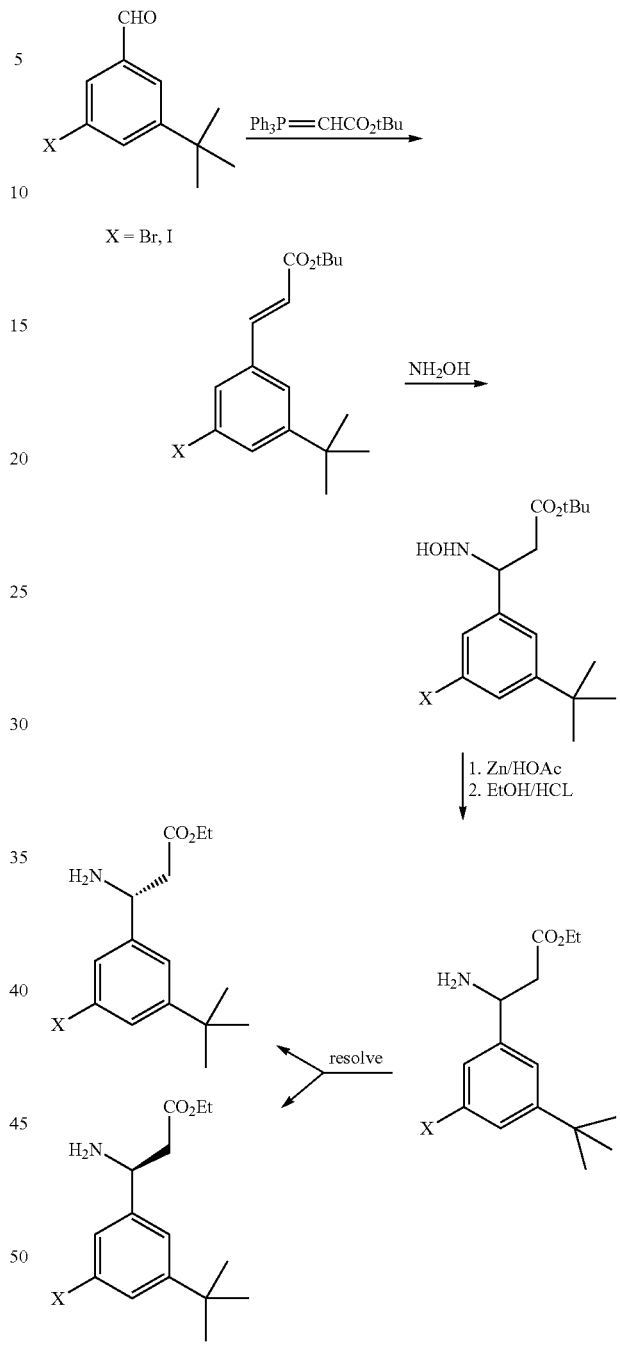

Scheme III illustrates an alternate general methodology for the synthesis of the beta amino acid ester portion of Formula I of the present invention, starting from the appropriate benzaldehyde. This beta amino acid ester can then be coupled to Boc-glycine followed by (after removal of the Boc protecting group) coupling to the benzoic acid described in Scheme I, or to the benzoic acid that has been coupled to glycine. Briefly, the appropriate benzaldehyde is converted to the corresponding cinnamate via the Wittig reaction. Michael addition of hydroxylamine to the resulting cinnamate affords the N-hydroxylated beta-amino acid ester. Reduction of the N-hydroxy-beta-amino acid ester with Zn/acetic acid gives, after conversion to the corresponding ethyl ester in EtOH/HCl, the desired beta amino acid ester as a racemate. As in Scheme II, these racemic beta amino acid esters can be resolved into the (R) and the preferred (S) enantiomers via chiral chromatographic separation (for example, via the CBZ derivative of the racemic ester, which is separated on a reverse phase chiral column, providing, after deprotection with, for example, TMSI, the pure (S) and (R) beta amino acid ester enantiomers) or via enzymatic resolution as described in Faulconbridge et al. (2000) or Landis et al. (2002).

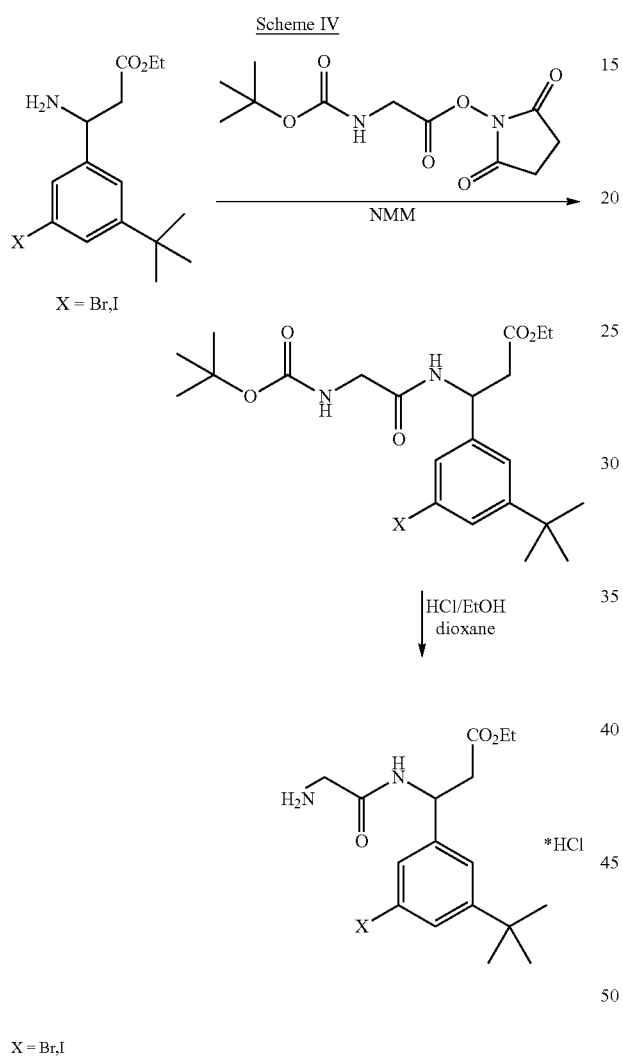

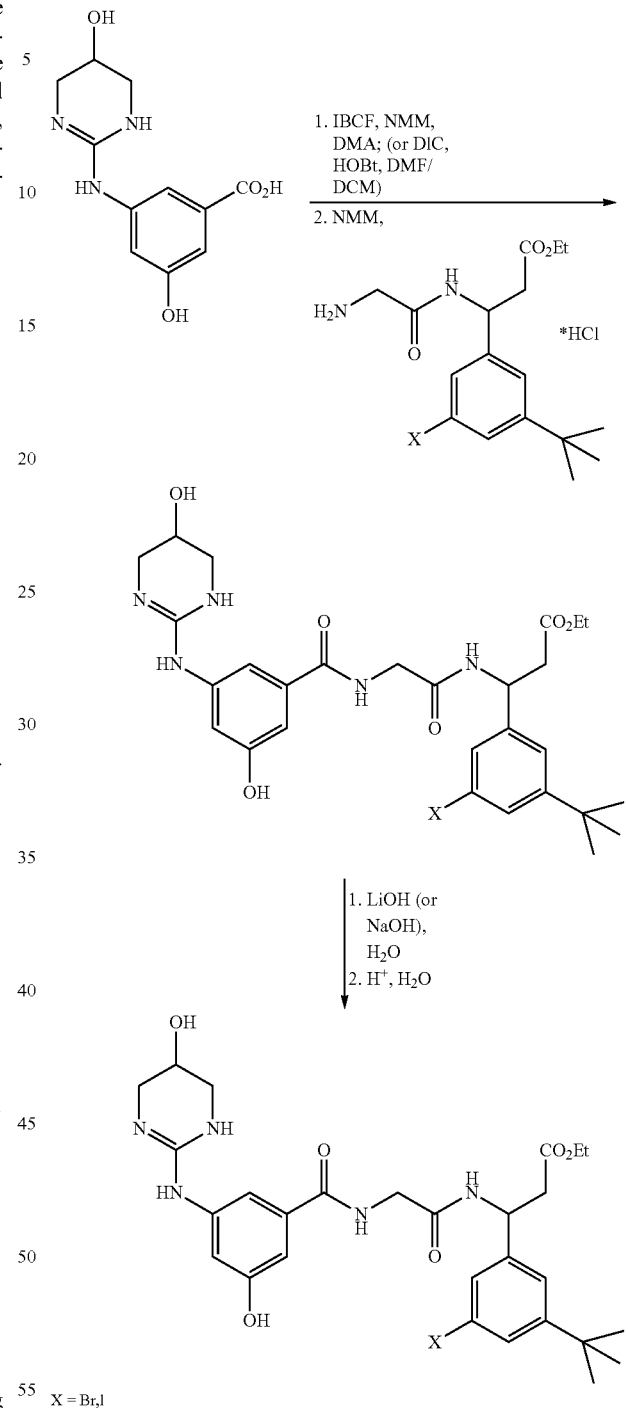

Scheme IV illustrates a general methodology for preparing the ethyl-N-gly-beta amino acid portion of Formula I of the present invention, which can be coupled to the benzoic acid portion of Formula I described in Scheme I. This method describes coupling a beta amino acid ester to glycine. Briefly, the desired beta amino acid ester (example methodologies described in Schemes II and III above) is treated with activated Boc glycine. Removal of the Boc protective group (by treatment with ethanol/HCl, for example) affords the glycine amide of the corresponding beta amino acid ester (the preferred (S) enantiomer is afforded by utilizing the (S)-beta amino acid ester, described in the above schemes).

Scheme V illustrates a general methodology useful for preparing the compounds of the present invention. Briefly, 3-Hydroxy-5-[(1,4,5,6-tetrahydro-5-hydroxy-2-pyrimidinyl)amino]benzoic acid (described for example in Scheme I) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added the gly-β-amino acid ester and NMM. Upon completion of the reaction the product is purified by prep HPLC and the ester hydrolyzed to the acid by treating with a base, such as LiOH in a suitable solvent (dioxane/water or acetonitrile/water). Alternatively, a suitable acid, such as TFA can be used. The product is isolated by prep HPLC or by isolating the zwitterion at pH 5-7 and converting to the desired salt by standard procedures. (The preferred (S) enantiomer is afforded by utilizing the (S)-beta amino acid ester, described in the above schemes).

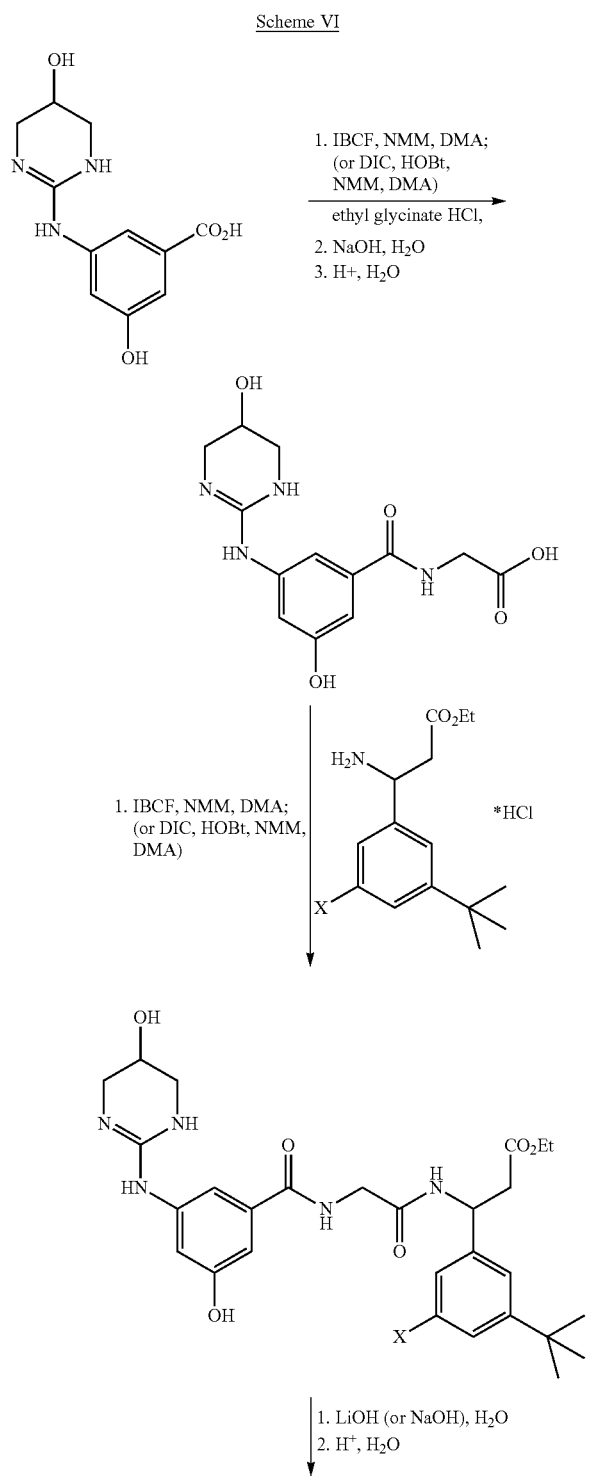

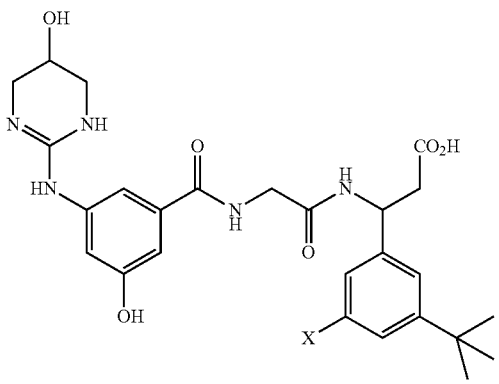

Scheme VI illustrates another general methodology useful for preparing the compounds of the present invention. Briefly, 3-Hydroxy-5-[(1,4,5,6-tetrahydro-5-hydroxy-2-pyrimidinyl)amino]benzoic acid (described for example in Scheme I) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added ethyl glycinate HCl and NMM. Upon completion of the reaction the product is purified by prep HPLC and the ester hydrolyzed to the acid by treating with a base, such as NaOH in a suitable solvent (water, dioxane/water or acetonitrile/water), followed by acidification. This gly adduct is then activated for coupling using known methods. Thus, after dissolving in a suitable solvent such as DMA an equivalent of NMM is added. The reaction mixture is cooled to ice-bath temperatures and IBCF added. To the mixed anhydride intermediate is added the appropriate beta amino acid ester salt (described, for example, in Schemes II and III above) and NMM. Upon completion of the reaction the product is purified by prep HPLC and the ester hydrolyzed to the acid by treating with a base, such as LiOH in a suitable solvent (dioxane/water or acetonitrile/water). Alternatively, a suitable acid, such as TFA can be used. The product is isolated by prep HPLC or by isolating the zwitterion at pH 5-7 and converting to the desired salt by standard procedures (the particular (S) enantiomer is afforded by utilizing the (S)-beta amino acid ester, described in the above schemes).

Scheme VII

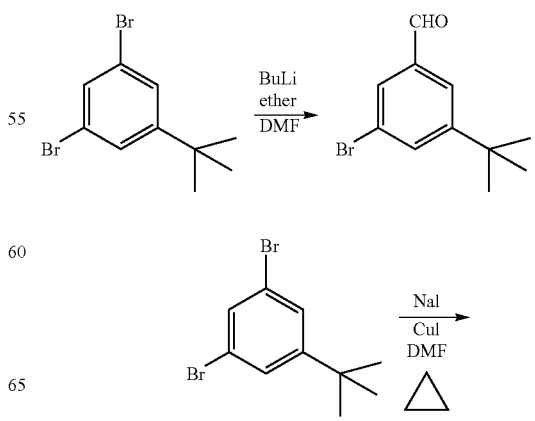

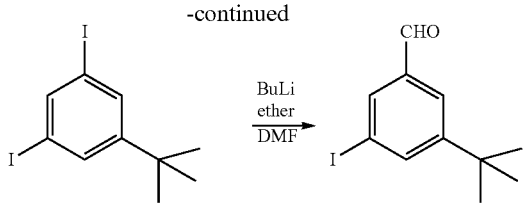

Scheme VII illustrates general synthetic methodologies for benzaldehyde starting materials that may not be readily available from commercial sources and that are useful for preparing the compounds of the present invention as described in the previous schemes. Such methods are well known in the art.

All these methods described above can be further modified and optimized using the principles and techniques of organic chemistry as applied by a person skilled in the art. Such principles and techniques are taught, for example, in *March's Advanced Organic Chemistry Reactions, Mechanisms, and Structure* (2007), which is incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The (S)-enantiomer of the beta amino acid portion of formula I is the preferred enantiomer. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration, as defined by the IUPAC 1974 Recommendations. For example, mixtures of stereoisomers may be separated using the techniques taught in the Examples section below, as well as modifications thereof. Tautomeric forms are also included as well as pharmaceutically acceptable salts of such isomers and tautomers.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like.

Examples of groups having an oxycarbonyl group include ethoxycarbonyl, tert-butoxycarbonyl (—C(O)OC(CH$_3$)$_3$, Boc), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. Biological Activity

It is another object of the invention to provide pharmaceutical compositions comprising compounds described above. Such compounds and compositions are useful in inhibiting or antagonizing integrins, and therefore in another embodiment, the present invention relates to a method of inhibiting or antagonizing the α5β1 integrin in particular, and additionally inhibiting or antagonizing the αvβ6 and αvβ8 integrins. Such compounds and compositions may be used to inhibit or antagonize additional integrins, such as αvβ3, αvβ5 and αvβ1 (herein defined as related integrins). The invention further involves treating or inhibiting pathological conditions associated therewith such as angiogenesis, including tumor angiogenesis, fibrosis and fibrotic diseases such as pulmonary fibrosis, renal, cardiac, and liver fibrosis, scleroderma, scarring, such as retinal, corneal and dermal scarring, retinopathy, including diabetic retinopathy and macular degeneration, vitreoretinopathy, including retinopathy of prematurity (ROP) and familial exudative vitreoretinopathy (FEVR), osteoporosis, humoral hypercalcemia of malignancy, Paget's disease, tumor metastasis, solid tumor growth (neoplasia), arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials. Further, such pharmaceutical agents are useful as immune system modulators via inhibition of TGF-β activation resulting from inhibiting or antagonizing the targeted integrins. Such immune modulation affects the immune activity and functions of T regulatory and T effector cells, and as such can be useful in the treatment of immune related pathologies, including autoimmune diseases such as multiple sclerosis, as well as in the treatment of tumors and infectious pathogens.

IV. Therapeutic Methods

The present invention relates to the fields of pharmaceuticals, medicine and cell biology. More specifically, it relates to pharmaceutical agents (compounds) which are useful as integrin receptor antagonists, with particularly exceptional biological activity as antagonists of the integrin α5b1, and additionally as exceptional antagonists of the integrins avb6 and avb8. As such, these compounds are useful in pharmaceutical compositions and in methods for treating conditions mediated by such integrins by inhibiting or antagonizing these integrins.

Certain compounds of the invention may combine α5β1 antagonism with antagonism of other RGD-binding integrins. Such mixed antagonists may be especially useful in treating or preventing diseases in which more than one integrin promotes aberrant angiogenesis. They may also be useful when a second disease process, which is either co-dependent or independent of angiogenesis, is mediated by RGD integrins that can be simultaneously affected with the anti-angiogenic antagonist. In particular, tumors are critically dependent on the formation of new blood vessels to sustain growth beyond a few millimeters in diameter. Aberrant angiogenesis in the retina is a characteristic of many blinding disorders such as wet age-related macular degeneration, vitreoretinopathies, retinopathy of prematurity, and diabetic retinopathy. Angiogenesis has been associated with progression of pulmonary and liver fibrosis, and with growth of the synovial pannus in rheumatoid arthritis.

The integrins αvβ3 and αvβ5 have been implicated in promoting angiogenesis (Avraamides et al., 2008), so that their antagonism in addition to α5β1 may be predicted to provide superior blockade of this process. Integrin αvβ3 is also known to play a role in tumor cell metastasis, and in the elevated bone resorption associated with osteoporosis and some cancers. The antagonists of the invention possess varying activity against at least five integrins that have been reported to bind the latent cytokine TGFβ complex in vitro: αvβ1, αvβ3, αvβ5, αvβ6, and αvβ8. See (Asano et al., 2005; Mu et al., 2002; Munger et al., 1999; Wipff et al., 2007; and Munger et al., 1998), which are incorporated herein by reference. TGFβ is frequently co-expressed with the angiogenic cytokine VEGF and induces its synthesis (Ferrari et al., 2006). Aside from having vascular regulatory activity, TGFβ is a powerful inducer of fibrosis in many tissues such as lung, liver, kidney, and skin (Nishimura, 2009). Virtually all TGFβ is secreted from cells in a complex which contains the latency associated peptide (LAP). The integrins αvβ3, αvβ5, and αvβ6, interact with the RGD motif contained within LAP, producing a conformational change in the complex which allows TGFβ to bind cellular receptors that activate pro-fibrotic pathways. Integrin αvβ8 also activates TGFβ in an RGD-dependent manner, but utilizes a protease-dependent mechanism distinct from the other integrins.

Latent TGFβ is ubiquitously present in tissues, and is activated by integrins in a spatially and temporally restricted manner. Therefore, upregulation of the epithelial integrin αvβ6 in the lungs or liver may promote localized collagen deposition and scarring, as has been observed in patients with idiopathic pulmonary fibrosis (Horan et al., 2008) or hepatic fibrosis (Popov et al., 2008). Similarly, αvβ5, and to a lesser extent αvβ3, are present on mesenchymal cells and are able to activate mesenchymal TGFβ (Wipff et al., 2007; Scotton et al., 2009). Integrin αvβ8 is expressed on subsets of epithelial, neural, immune, and mesenchymal cell types. In the skin, the TGFβ activation that accompanies the wound healing process mediates matrix deposition and promotes the formation of scars. Compounds of this invention, by virtue of their ability to simultaneously inhibit several TGFβ-activating integrins, have potential for greater efficacy in treatment of fibrosis than any previously described compounds having more restricted inhibitory profiles. Furthermore, these compounds which have exceptional α5β1 potency, have unique potential for benefit in diseases characterized by both aberrant angiogenic and fibrotic pathologies.

TGFβ is an important inducer of the formation of FoxP3+ regulatory T cells ($T_{reg}$) (Yoshimura, 2011). Therefore, compounds of the present invention that inhibit the activation of TGFβ may reduce $T_{reg}$ activity, and in turn relieve immune suppression in disease states such as cancer, when administered alone or in combination with existing therapies. Mitigation of $T_{reg}$ activity with such compounds also has the potential to enhance the activity of vaccines which are intended to prevent or treat cancer and infectious diseases. TGFβ, in the presence of IL-6, promotes the conversion of naïve T cells to TH17 cells (Yoshimura, 2011). These cells promote a variety of autoimmune diseases. It has been reported that mice lacking all αvβ8 expression on dendritic cells have near complete protection from experimental autoimmune encephalitis, a model of multiple sclerosis (Melton et al., 2010). Therefore, compounds of the present invention that inhibit the activation of TGFβ may reduce Th17 activity, and be useful in preventing or treating autoimmune disease when administered alone or in combination with existing therapies.

Antagonism of the integrin αIIbβ3 (also known as the fibrinogen receptor), is known to block platelet aggregation as part of the blood coagulation process. Hence, to avoid increased bleeding when treating conditions or disease states mediated by integrin α5β1 and other integrins, it would be beneficial to utilize compounds which selectively spare αIIbβ3. A role for αvβ5 in normal maintenance of the retina has also been described (Nandrot et al., 2006). Therefore, in some uses of compounds, it may be desirable to spare αvβ5 inhibition.

As discussed above, integrins are a family of integral cytoplasmic membrane proteins that mediate cell interactions with other cells and with the extracellular matrix (ECM). They also play a role in cell signaling and thereby regulate cellular shape, motility, and the cell cycle. Not only do integrins perform "outside-in" signaling typical of receptors, but they also operate an "inside-out" mode. Thus, they transduce information from the ECM to the cell as well as reveal the status of the cell to the outside, allowing rapid and flexible responses to changes in the environment, for example to allow blood coagulation by platelets.

There are many types of integrin, and many cells have multiple types on their surface. Integrins are of vital importance to all animals and have been found in all animals investigated, from sponges to mammals. Integrins have been extensively studied in humans. Integrins work alongside other proteins such as cadherins, immunoglobulin superfamily cell adhesion molecules, selectins and syndecans to mediate cell-cell and cell-matrix interaction and communication. Integrins bind cell surface and ECM components such as fibronectin, vitronectin, collagen, and laminin.

When released into the cell membrane, newly synthesized integrin dimers are speculated to be found in the same "bent" conformation revealed by the structural studies described above. One school of thought claims that this bent form prevents them from interacting with their ligands, although bent forms can predominate in high-resolution EM structures of integrin bound to an ECM ligands. Therefore, integrin dimers must apparently not be 'unbent' in order to prime them and allow their binding to the ECM. In cells, the priming is accomplished by a protein named Talin, which binds to the β tail of the integrin dimer and changes its conformation. Moreover, talin proteins are able to dimerize and thus are thought to intervene in the clustering of integrin dimers which leads to the formation of a focal adhesion. Recently, the Kindlin-1 and Kindlin-2 proteins have also been found to interact with integrin and activate it.

Each integrin is formed by the non-covalent heterodimerization of alpha and beta glycoprotein subunits, the combination of which conveys distinct biological activities such as cell attachment, proliferation, migration, differentiation, and survival. Currently, 24 integrins have been described in mammals that are formed by pairing of 18 α subunits and 8 β subunits:

TABLE 1

Integrins

| Gene | Protein | Synonym | Type |
|---|---|---|---|
| ITGA1 | CD49a | VLA1 | Alpha |
| ITGA2 | CD49b | VLA2 | Alpha |
| ITGA3 | CD49c | VLA3 | Alpha |
| ITGA4 | CD49d | VLA4 | Alpha |
| ITGA5 | CD49e | VLA5 | Alpha |
| ITGA6 | CD49f | VLA6 | Alpha |
| ITGA7 | ITGA7 | FLJ25220 | Alpha |
| ITGA8 | ITGA8 | | Alpha |
| ITGA9 | ITGA9 | RLC | Alpha |
| ITGA10 | ITGA10 | | Alpha |
| ITGA11 | ITGA11 | HsT18964 | Alpha |
| ITGAD | CD11D | FLJ39841 | Alpha |
| ITGAE | CD103 | HUMINAE | Alpha |
| ITGAL | CD11a | LFA1A | Alpha |
| ITGAM | CD11b | MAC-1 | Alpha |
| ITGAV | CD51 | VNRA, MSK8 | Alpha |
| ITGAW | ITGAW | | Alpha |
| ITGAX | CD11c | | Alpha |
| ITGB1 | CD29 | FNRB, MSK12, MDF2 | Beta |
| ITGB2 | CD18 | LFA-1, MAC-1, MFI7 | Beta |
| ITGB3 | CD61 | GP3A, GPIIIa | Beta |
| ITGB4 | CD104 | | Beta |
| ITGB5 | ITGB5 | FLJ26658 | Beta |
| ITGB6 | ITGB6 | | Beta |
| ITGB7 | ITGB7 | | Beta |
| ITGB8 | ITGB8 | | Beta |

In addition, variants of some of the subunits are formed by differential splicing; for example, four variants of the beta-1 subunit exist. Through different combinations of these α and β subunits, some 24 unique integrins are generated, although the number varies according to different studies.

Integrin subunits span the plasma membrane and in general have very short cytoplasmic domains of about 40-70 amino acids. The exception is the beta-4 subunit, which has a cytoplasmic domain of 1088 amino acids, one of the largest known cytoplasmic domains of any membrane protein. Outside the cell plasma membrane, the α and β chains lie close together along a length of about 23 nm; the final 5 nm N-termini of each chain forms a ligand-binding region for the extracellular matrix (ECM).

The molecular mass of the integrin subunits can vary from 90 kDa to 160 kDa. Beta subunits have four cysteine-rich repeated sequences. Both α and β subunits bind several divalent cations. The role of divalent cations in the α subunit is unknown, but may stabilize the folds of the protein. The cations in the β subunits are more interesting: they are directly involved in coordinating at least some of the ligands that integrins bind.

There are various ways of categorizing the integrins. For example, a subset of the α chains has an additional structural element (or "domain") inserted toward the N-terminal, the alpha-A domain (so called because it has a similar structure to the A-domains found in the protein von Willebrand factor; it is also termed the α-I domain). Integrins carrying this domain either bind to collagens (e.g., integrins α1 β1, and α2 β1), or act as cell-cell adhesion molecules (integrins of the β2 family). This α-I domain is the binding site for ligands of such integrins. Those integrins that don't carry this inserted domain also have an A-domain in their ligand binding site, but this A-domain is found on the β subunit.

In both cases, the A-domains carry up to three divalent cation binding sites. One is permanently occupied in physiological concentrations of divalent cations, and carries either a calcium or magnesium ion, the principal divalent cations in blood at median concentrations of 1.4 mM (calcium) and 0.8 mM (magnesium). The other two sites become occupied by cations when ligands bind—at least for those ligands involving an acidic amino acid in their interaction sites. An acidic amino acid features in the integrin-interaction site of many ECM proteins, for example as part of the amino acid sequence Arginine-Glycine-Aspartic acid ("RGD").

The invention also relates to a method of inhibiting or antagonizing the α5β1 integrin in particular, as well as αvβ6 and αvβ8 and related integrins. More specifically, it relates to a method of inhibiting pathological conditions associated therewith such as angiogenesis, including tumor angiogenesis, fibrosis and fibrotic diseases such as pulmonary, renal, cardiac and liver fibrosis, scarring, such as retinal, corneal and dermal scarring, retinopathy, including diabetic retinopathy and macular degeneration, vitreoretinopathy, including retinopathy of prematurity (ROP) and familial exudative vitreoretinopathy (FEVR), osteoporosis, humoral hypercalcemia of malignancy, Paget's disease, tumor metastasis, solid tumor growth (neoplasia), arthritis, including rheumatoid arthritis, periodontal disease, psoriasis, smooth muscle cell migration and restenosis, autoimmune disease, such as multiple sclerosis, and infectious pathogens by administering a therapeutically effective amount of a compound described above to achieve such inhibition together with a pharmaceutically acceptable carrier.

For the selective inhibition or antagonism of α5b1, avb6, avb8 and related integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitoneally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by inhibiting or antagonizing the α5b1, avb6, avb8 and related cell surface integrin receptors, which method comprises administering a therapeutically effective amount of a compound selected from the class of compounds described above, wherein one or more compounds is administered in association with one or more nontoxic, pharmaceutically acceptable carriers and/or diluents and/or adjuvants (collectively referred to herein as "carrier" materials) and if desired other active ingredients. More specifically, the present invention provides a method for inhibition of the α5b1, avb6, avb8 and related cell surface integrin receptors. Most preferably the present invention provides a method for inhibiting angiogenesis, including tumor angiogenesis, inhibiting and treating fibrosis and fibrotic diseases such as pulmonary fibrosis and liver fibrosis, inhibiting and treating scarring, such as retinal, corneal and dermal scarring, inhibiting and treating retinopathy, including diabetic retinopathy and macular degeneration, inhibiting and treating vitreoretinopathy, including retinopathy of prematurity (ROP) and familial exudative vitreoretinopathy (FEVR), inhibiting bone resorption, treating osteoporosis, treating humoral hypercalcemia of malignancy, treating Paget's disease, inhibiting tumor metastasis, inhibiting solid tumor growth (neoplasia), treating arthritis, including rheumatoid arthritis, treating periodontal disease, treating psoriasis, inhibiting smooth muscle cell migration and restenosis, treating autoimmune disease, such as multiple sclerosis, and inhibiting and treating infectious pathogens.

Based upon standard laboratory experimental techniques and procedures well known and appreciated by those skilled in the art, as well as comparisons with compounds of known usefulness, the compounds described above can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

As stated previously, the compounds of the invention can be used in a variety of biological, prophylactic or therapeutic areas. It is contemplated that these compounds are useful in prevention or treatment of any disease state or condition wherein the α5b1, avb6, avb8 and related integrins plays a role.

V. Pharmaceutical Formulations and Routes of Administration

For administration to a mammal in need of such treatment, the compounds in a therapeutically effective amount are ordinarily combined with one or more excipients appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Instrumentation and General Methods.

Chemical ionization mass spectra were recorded, at 70 eV ionizing voltage, on a Hewlett-Packard 5973 CI quadrupole mass spectrometer connected to a Hewlett-Packard 6890 gas chromatograph fitted with a Agilent Tech 12 m×0.2 mm×0.33 μm DB-1 (cross linked methyl silicone) column.

Example A

Preparation of 3-Hydroxy-5-((5-hydroxy-1,4,5,6-tetrahydropyrimidin-2-yl)aminobenzoic acid

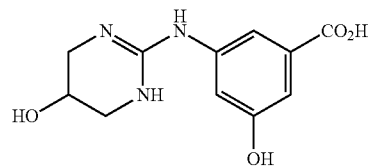 [SMILES: O=C(O)c1cc(O)cc(NC2=NCC(O)CN2)c1]

3-Hydroxy-5-((5-hydroxy-1,4,5,6-tetrahydropyrimidin-2-yl)aminobenzoic acid was synthesized according to literature procedures (see *Organic Process Research & Development*, 2004).

Example B

Preparation of 2-(3-Hydroxy-5-((5-hydroxy-1,4,5,6-tetrahydropyrimidin-2-yl)amino)benzamido) acetic acid

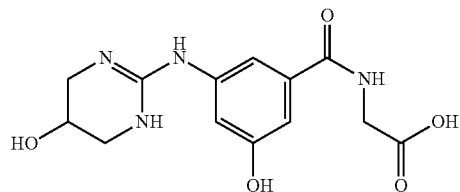 [SMILES: O=C(O)CNC(=O)c1cc(O)cc(NC2=NCC(O)CN2)c1]

2-(3-Hydroxy-5-((5-hydroxy-1,4,5,6-tetrahydropyrimidin-2-yl)amino)benzamido)acetic acid was prepared by the following procedure:

Coupling of 3-hydroxy-5-((5-hydroxy-1,4,5,6-tetrahydropyrimidin-2-yl)aminobenzoic acid with glycine ethyl ester

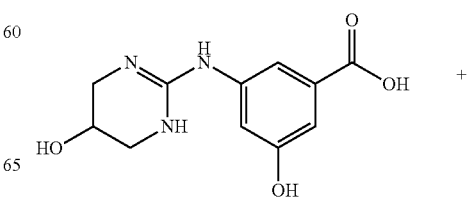

-continued

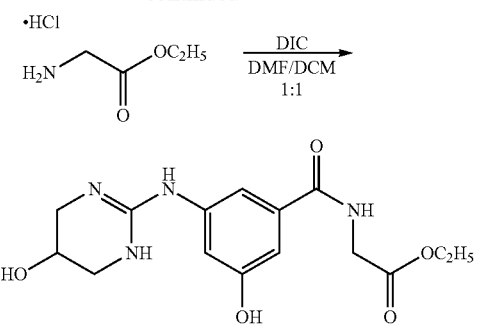

To a suspension of 3-hydroxy-5-((5-hydroxy-1,4,5,6-tetrahydropyrimidin-2-yl)aminobenzoic acid (9.013 g, 35.87 mmol) in a 1:1 mixture of DMF (50.0 mL) and DCM (50.0 mL) was added glycine ethyl ester hydrochloride (5.02 g, 35.95 mmol) and the mixture was stirred at room temperature under nitrogen atmosphere. Neat N,N'-diisopropylcarbodiimide (6.75 mL, 43.60 mmol) was added to above reaction mixture and the mixture was stirred at room temperature overnight to give a colorless suspension. The crude reaction mixture was used as such for the hydrolysis of the above ester.

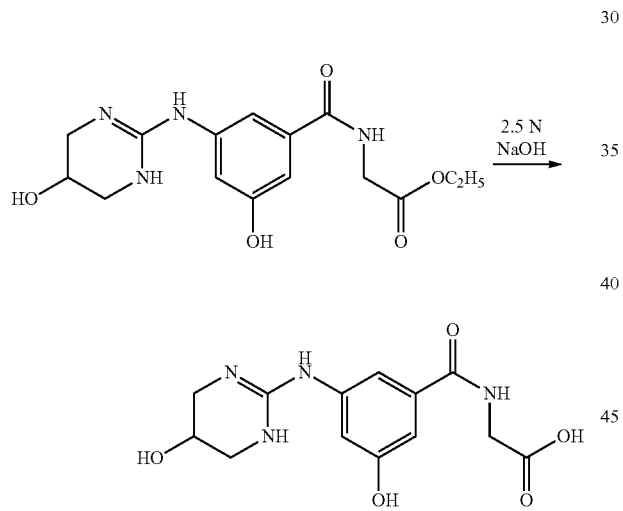

The above crude reaction mixture was cooled to 10° C. (ice-bath) and a 2.5 N NaOH solution (90.0 mL) was added slowly with stirring, the solution temperature was kept below 20° C., to give a pale yellow solution/suspension. The reaction mixture was stirred at room temperature for 1.5 h. The reaction mixture was acidified with 5N HCl with stirring to pH 5 to give a colorless precipitate and the mixture was stirred at room temperature for another 15 min and filtered to give a colorless solid. The solid was washed with water (1×25 mL) and then with acetonitrile (1×25 mL). The solid was dried in vacuo to give a colorless powder (9.686 g, yield 88%).

$^1$H NMR (400 MHz, D$_2$O): δ 3.37 (dd, J=12.7 and 3.1 Hz, 2H), 3.50 (dd, J=12.7 and 2.8 Hz, 2H), 4.17 (s, 2H), 4.37 (m, 1H), 6.97 (t, J=2.01 Hz, 1H), 7.17-7.26 (m, 2H). $^1$H NMR spectrum of the sample was consistent with the suggested structure of the product.

Example 1

Preparation of (3S)—N-[3-hydroxy-5-[(1,4,5,6-tetrahydro-5-hydroxy-2-pyrimidinyl)amino]benzoyl] glycyl-3-(3-bromo-5-tert-butylphenyl)-β-alanine

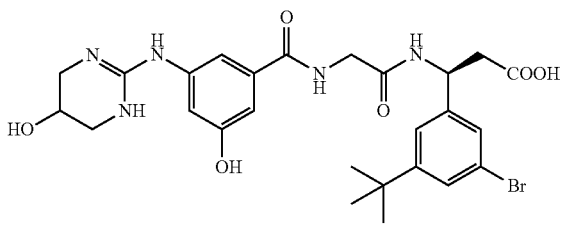 [SMILES: CC(C)(C)c1cc(Br)cc([C@H](CC(=O)O)NC(=O)CNC(=O)c2cc(O)cc(NC3=NCC(O)CN3)c2)c1]

Preparation of (S)-ethyl 3-amino-3-(3-bromo-5-tert-butylphenyl)propionate hydrochloride Step #1

Preparation of 3-bromo-5-tert-butylbenzaldehyde

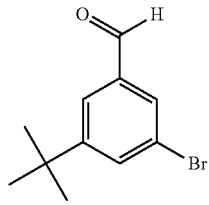

1,3-Dibromo-5-tert-butylbenzene (4.95 g, 16.95 mmol) was dissolved in anhydrous ether (25.0 mL) in a dried flask under nitrogen. The reaction mixture was cooled to −78° C. and stirred under nitrogen atmosphere. A 1.6 M solution of n-BuLi in hexanes (10.60 mL, 16.95 mmol) was added dropwise to the above solution and the reaction mixture was stirred at −78° C. for 30 min after complete addition of n-BuLi. After 30 min of stirring at −78° C., the reaction mixture was warmed to −30° C. DMF (1.60 mL, 20.66 mmol) was added to above reaction mixture dropwise, keeping the reaction mixture below −20° C. After addition of DMF is complete, the reaction mixture was warmed slowly to 0° C. (30 min) and then stirring at room temperature overnight under nitrogen to give a yellow-orange solution. The reaction mixture was poured into 40 mL of chilled 10% aqueous HCl and the reaction mixture was stirred for 15 min. The ether layer was separated, washed with water (2×25 mL), dried over anhydrous MgSO$_4$, filtered and evaporated in vacuo to give the product as a pale yellow viscous liquid. The crude product was dissolved in dichloromethane (25.0 mL) and passed through a small pad of silica gel (~100 mg). Evaporation of the solvent in vacuo gave the product as a very pale yellow viscous liquid (4.096 g). GC-MS analysis (CI mode/ methane) shows the desired product's mass: m/z 240 ($^{79Br}$M$^+$) and m/z 242 ($^{81Br}$M$^+$); Calcd for C$_{11}$H$_{13}$BrO: 241.12.

Step #2

Preparation of 3-amino-3-(3-bromo-5-tert-butylphenyl)propionic acid

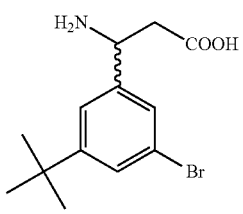 [SMILES: CC(C)(C)c1cc(Br)cc(C(N)CC(=O)O)c1]

A suspension of 3-bromo-5-tert-butylbenzaldehyde (4.17 g, 17.30 mmol), malonic acid (2.15 g, 20.72 mmol) and ammonium acetate (2.66 g, 34.59 mmol) in isopropanol (35 mL) was heated at reflux under nitrogen for 3 h to afford a thick colorless solid. The solid was filtered hot, washed with hot isopropanol (2×25 mL) and dried in vacuo to give the desired racemic product as a colorless solid (2.68 g).

Step #3

Preparation of ethyl 3-amino-3-(3-bromo-5-tert-butylphenyl) propionate hydrochloride

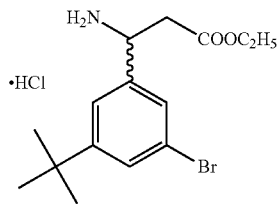

Absolute ethanol saturated with anhydrous HCl gas (75 mL) was added to 3-amino-3-(3-bromo-5-tert-butylphenyl)propionic acid (4.78 g, 15.92 mmol) and the reaction mixture was heated at reflux for 1.5 h to give a pale yellow solution. The solvent was removed in vacuo to give a colorless solid. The solid was slurried with diethyl ether and heptane (2×25 mL). After the solvent layer was decanted off, the residue was dried in vacuo to give the racemic β-amino ester hydrochloride salt as a cream solid (5.00 g).

Step #4

Preparation of (S)-ethyl 3-amino-3-(3-bromo-5-tert-butylphenyl)propionate hydrochloride Enzymatic resolution of the racemic mixture

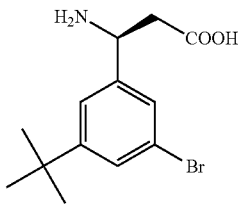 [SMILES: CC(C)(C)c1cc(Br)cc([C@@H](N)CC(=O)O)c1]

A suspension of ethyl 3-amino-3-(3-bromo-5-tert-butylphenyl)propionate hydrochloride (4.54 g, 12.45 mmol) in water (10.0 mL) was basified with 2.5N NaOH (pH ~12) by dropwise addition to give a creamy oily residue. The pH of the aqueous layer was adjusted to pH 8.20 by the addition of 50 mM $KH_2PO_4$ solution. Amano lipase PS (5.24 g) was added to above reaction mixture and the reaction mixture was stirred at room temperature overnight. The reaction mixture was filtered after 22 h and the solid was washed with acetone to give a colorless solid of the resolved (S)-acid (1.72 g).

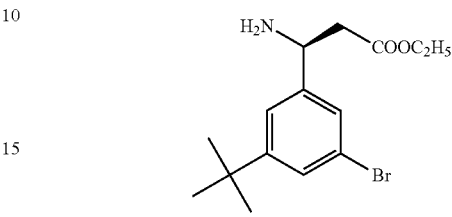

Absolute ethanol saturated with anhydrous HCl gas (35 mL) was added to (S)-3-amino-3-(3-bromo-5-tert-butylphenyl)propionic acid (1.83 g, 6.10 mmol) and the reaction mixture was heated at reflux for 2 h to give a colorless solution. The solvent was removed in vacuo to give a cream-yellow foamy solid. The solid was slurried with heptane. After the solvent was decanted off, the residue was dried in vacuo to give the desired (S)-β-amino ester hydrochloride salt as a pale yellow foamy solid (2.26 g).

Step #5

Preparation of (3S)—N-[3-hydroxy-5-[(1,4,5,6-tetrahydro-5-hydroxy-2-pyrimidinyl)amino]benzoyl]glycyl-3-(3-bromo-5-tert-butylphenyl)-β-alanine Example 1

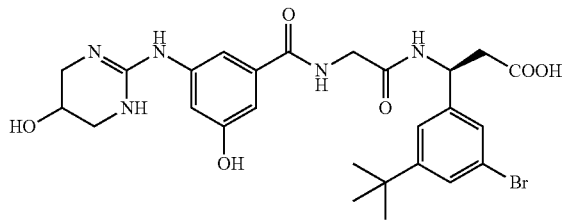 [SMILES: CC(C)(C)c1cc(Br)cc([C@H](CC(=O)O)NC(=O)CNC(=O)c2cc(O)cc(NC3=NCC(O)CN3)c2)c1]

A mixture of 2-(3-hydroxy-5-((5-hydroxy-1,4,5,6-tetrahydropyrimidin-2-yl)amino)benzamido)acetic acid (Example B) (1.92 g, 6.23 mmol), and (S)-ethyl 3-amino-3-(3-bromo-5-tert-butylphenyl) propionate hydrochloride (2.25 g, 6.17 mmol) was dissolved in DMF (20.0 mL) and dichloromethane (10.0 mL) to give a cream suspension. 1-hydroxybenzatriazole hydrate was added to above reaction mixture and the reaction mixture was stirred in an ice-bath under nitrogen atmosphere for 10 min. N,N'-diisopropylcarbodiimide (DIC) was added and the reaction mixture was stirred at room temperature overnight under nitrogen atmosphere. The solvent was evaporated in vacuo to give a pale yellow viscous gummy residue. The residue was dissolved in acetonitrile (50 mL) and filtered to remove precipitated urea. Evaporation of the filtrate in-vacuo afforded a pale yellow to cream foamy residue of the crude (3S)—N-[3-hydroxy-5-[(1,4,5,6-tetrahydro-5-hydroxy-2-pyrimidinyl)imino]benzoyl]glycyl-3-(3-bromo-5-tert-butylphenyl)-β-alanine ethyl ester. To a suspension of the crude ester in a 1:1 mixture of water/ acetonitrile (14.0 mL) was added lithium hydroxide monohydrate (2.07 g, 49.38 mmol) at room temperature and the reaction mixture was stirred at room temperature for 1.5 h. The reaction mixture was acidified with TFA and evaporated in vacuo to give a cream foamy solid. The solid was purified by reverse-phase preparative HPLC (10-90% water/acetonitrile containing 0.05% TFA) to afford the desired product, after lyophilization, as a colorless powder (2.244 g). LC/MS shows the desired product's mass: m/z 590 ($^{79Br}$M+H) and 592 ($^{81Br}$M+H); Calcd for $C_{26}H_{32}BrN_5O_6$: 590.47. $^1$H NMR (400 MHz, DMSO-$d_6$): δ 1.27 (s, 9H, $(CH_3)_3C$—), 2.70 (d, J=7.31 Hz, 2H, —$CH_2$—COOH), 3.16 (dd, J=12.22, 3.10 Hz, 2H), 3.33 (brd, J=12.44 Hz, 2H), 3.87 (d, J=5.81 Hz, 2H), 4.08 (appt/m, J=2.92 Hz, 1H), 5.18 (q, J=7.62 Hz, 1H, —NH—CH—$CH_2$—COOH), 6.75 (t, J=2.03 Hz, 1H), 7.13 (dt, J=10.70 and 1.50 Hz, 2H), 7.34 (dt, J=9.54 and 1.50 Hz, 2H), 7.39 (appt, J=1.72 Hz, 1H), 8.09 (brs, 2H), 8.51 (d, J=8.30 Hz, 1H), 8.61 (brt, J=5.88 Hz, 1H), 9.57 (s, 1H), 10.00 (brs, 1H), 12.35 (brs, 1H, —COOH). $^1$H NMR spectrum of the sample was consistent with the suggested structure of the product.

Example 2

Biological Assay Results

The activity of the compounds of the present invention was tested in the following assays. The results of testing in the assays are shown in Table 2.

K562 Cell Adhesion Assay for α5β1 Function.

Purified human plasma fibronectin (Calbiochem/EMD Biosciences) diluted to 5 µg/ml in TS buffer (25 mM Tris 7.4, 150 mM NaCl) was added to wells (100 µl/well) of a 96-well microtiter plate (Immulon 2HB 96-well; VWR Scientific) and incubated overnight at 4° C. The solution in each well was then replaced with 200 µl of blocking buffer (TS with 1% bovine serum albumin), and the plate incubated for 1 hr at 37° C. Compounds were diluted in test tubes to 2× the peak testing concentration in cell adhesion buffer consisting of Hanks Buffered Salts Solution (HBSS, cation-free, Sigma), 0.1% bovine serum albumin, 25 mM HEPES, and 200 µM $MnCl_2$. Serial 1:3 dilutions were them made into tubes containing the cell adhesion buffer. In separate tubes, anti-integrin α5β1 neutralizing antibody 11A1 (BD Biosciences) and isotype-matched negative control antibody MOPC21 (Sigma) were diluted to 2 µg/ml with cell adhesion buffer. In another tube, EDTA was diluted to 5 mM in the cell adhesion buffer. Human erythroleukemia K562 cells (American Type Culture Collection, Manassas, Va.) which naturally express high levels of α5β1 were detached from culture using non-enzymatic Cell Dissociation Solution (Sigma). The cells were washed with the cell adhesion buffer, counted using a hemocytometer, centrifuged and resuspended in cell adhesion buffer at 3×10$^6$ cells/ml. Equal volumes of the cell suspension were then mixed with the diluted compound and control solutions. The tubes were incubated at 30 min at 37° C. After washing the ligand-coated plates 3× with cell adhesion buffer, 100 µl of the pre-treated cell samples were added to wells, with each sample repeated in triplicate, according to a standard plate template. Plates were incubated for 30 min at 37° C. to allow cell adhesion, and then unbound cells were gently removed by washing 3× with cell adhesion buffer. Remaining attached cells were detected by addition of 100 µl/well p-nitrophenylphosphate (Sigma) solution (15 mg tablet dissolved in 25 ml 50 mM NaAcetate, pH 5; 0.5% Triton-X-100), incubation for 30 min at 37° C., and then addition of 50 µl/well 1N NaOH to stop the enzyme reaction. Plates were read by colorimetric detection at 405 nm wavelength using a Tecan Safire II plate reader. Concentration-response curves were constructed by non-linear regression (best fit) analysis, and $IC_{50}$ values were calculated for each compound. EDTA and antibody control samples were evaluated to confirm integrin, and more specifically α5β1-dependent cell binding in each assay.

HT-29 Cell Adhesion Assay for αvβ6 Function.

Purified human LAP protein (R&D Systems, Inc) diluted to 0.2 µg/ml in TS buffer (25 mM Tris 7.4, 150 mM NaCl) was added to wells (100 µl/well) of a 96-well microtiter plate (Immulon 2HB 96-well; VWR Scientific) and incubated overnight at 4° C. The solution in each well was then replaced with 200 µl of blocking buffer (TS with 1% bovine serum albumin), and the plate incubated for 1 hr at 37° C. Compounds were diluted in test tubes to 2× the peak testing concentration in cell adhesion buffer consisting of Hanks Buffered Salts Solution (HBSS, cation-free, Sigma), 0.1% bovine serum albumin, 25 mM HEPES, and 200 µM $MnCl_2$. Serial 1:3 dilutions were them made into tubes containing the cell adhesion buffer. In separate tubes, anti-integrin αvβ6 neutralizing antibody 10D5 (Millipore) and isotype-matched negative control antibody UPC-10 (Sigma) were diluted to 2 µg/ml with cell adhesion buffer. In another tube, EDTA was diluted to 5 mM in the cell adhesion buffer. Human colon adenocarcinoma HT-29 cells (American Type Culture Collection, Manassas, Va.), which naturally express αvβ6, were detached from culture using non-enzymatic Cell Dissociation Solution (Sigma). The cells were washed with the cell adhesion buffer, counted using a hemocytometer, centrifuged and resuspended in cell adhesion buffer at 4×10$^6$ cells/ml. Equal volumes of the cell suspension were then mixed with the diluted compound and control solutions. The tubes were incubated at 30 min at 37° C. After washing the ligand-coated plates 3× with cell adhesion buffer, 100 µl of the pre-treated cell samples were added to wells, with each sample repeated in triplicate, according to a standard plate template. Plates were incubated for 30 min at 37° C. to allow cell adhesion, and then unbound cells were gently removed by washing 3× with cell adhesion buffer. Remaining attached cells were detected by addition of 100 µl/well p-nitrophenylphosphate (Sigma) solution (15 mg tablet dissolved in 25 ml 50 mM NaAcetate, pH5; 0.5% Triton-X-100), incubation for 30 min at 37° C., and then addition of 50 µl/well 1N NaOH to stop the enzyme reaction. Plates were read by colorimetric detection at 405 nm wavelength using a Tecan Safire II plate reader. Concentration-response curves were constructed by non-linear regression (best fit) analysis, and $IC_{50}$ values were calculated for each compound. EDTA and antibody control samples were evaluated to confirm integrin, and more specifically αvβ6-dependent cell binding in each assay.

293/b3 Cell Adhesion Assay for αvβ3 Function.

Purified human vitronectin (Calbiochem/EMD Biosciences) diluted to 0.25 µg/ml in TS buffer (25 mM Tris 7.4, 150 mM NaCl) was added to wells (100 µl/well) of a 96-well microtiter plate (Immulon 2HB 96-well; VWR Scientific) and incubated overnight at 4° C. The solution in each well was then replaced with 200 µl of blocking buffer (TS with 1% bovine serum albumin), and the plate incubated for 1 hr at 37° C. Compounds were diluted in test tubes to 2× the peak testing concentration in cell adhesion buffer consisting of Hanks Buffered Salts Solution (HBSS, cation-free, Sigma), 0.1% bovine serum albumin, 25 mM HEPES, and 200 µM $MnCl_2$. Serial 1:3 dilutions were them made into tubes containing the cell adhesion buffer. In separate tubes, anti-integrin αvβ3 neutralizing antibody LM609 (Millipore) and isotype-matched negative control antibody MOPC21 (Sigma) were diluted to 2 µg/ml with cell adhesion buffer. In another tube, EDTA was diluted to 5 mM in the cell adhesion buffer. Recombinant human embryonic kidney cells 293/b3, which have been transfected to constitutively overexpress αvβ3 (Engleman et al., 1997), were detached from culture using non-enzymatic Cell Dissociation Solution (Sigma). The cells were washed with the cell adhesion buffer, counted using a hemocytometer, centrifuged and resuspended in cell adhesion buffer at $3\times10^6$ cells/ml. Equal volumes of the cell suspension were then mixed with the diluted compound and control solutions. The tubes were incubated at 30 min at 37° C. After washing the ligand-coated plates 3× with cell adhesion buffer, 100 µl of the pre-treated cell samples were added to wells, with each sample repeated in triplicate, according to a standard plate template. Plates were incubated for 30 min at 37° C. to allow cell adhesion, and then unbound cells were gently removed by washing 3× with cell adhesion buffer. Remaining attached cells were detected by addition of 100 µl/well p-nitrophenylphosphate (Sigma) solution (15 mg tablet dissolved in 25 ml 50 mM NaAcetate, pH5; 0.5% Triton-X-100), incubation for 30 min at 37° C., and then addition of 50 µl/well 1N NaOH to stop the enzyme reaction. Plates were read by colorimetric detection at 405 nm wavelength using a Tecan Safire II plate reader. Concentration-response curves were constructed by non-linear regression (best fit) analysis, and $IC_{50}$ values were calculated for each compound. EDTA and antibody control samples were evaluated to confirm integrin, and more specifically αvβ3-dependent cell binding in each assay.

293/b5 Cell Adhesion Assay for αvβ5 Function.

Purified human vitronectin (Calbiochem/EMD Biosciences) diluted to 0.25 µg/ml in TS buffer (25 mM Tris 7.4, 150 mM NaCl) was added to wells (100 µl/well) of a 96-well microtiter plate (Immulon 2HB 96-well; VWR Scientific) and incubated overnight at 4° C. The solution in each well was then replaced with 200 µl of blocking buffer (TS with 1% bovine serum albumin), and the plate incubated for 1 hr at 37° C. Compounds were diluted in test tubes to 2× the peak testing concentration in cell adhesion buffer consisting of Hanks Buffered Salts Solution (HBSS, cation-free, Sigma), 0.1% bovine serum albumin, 25 mM HEPES, and 200 µM $MnCl_2$. Serial 1:3 dilutions were them made into tubes containing the cell adhesion buffer. In separate tubes, anti-integrin αvβ5 neutralizing antibody P1F6 (Millipore) and isotype-matched negative control antibody MOPC21 (Sigma) were diluted to 2 µg/ml with cell adhesion buffer. In another tube, EDTA was diluted to 5 mM in the cell adhesion buffer. Recombinant human embryonic kidney cells 293/b5, which have been transfected to constitutively overexpress αvβ5 (Engleman et al., 1997), were detached from culture using non-enzymatic Cell Dissociation Solution (Sigma). The cells were washed with the cell adhesion buffer, counted using a hemocytometer, centrifuged and resuspended in cell adhesion buffer at $3\times10^6$ cells/ml. Equal volumes of the cell suspension were then mixed with the diluted compound and control solutions. The tubes were incubated at 30 min at 37° C. After washing the ligand-coated plates 3× with cell adhesion buffer, 100 µl of the pre-treated cell samples were added to wells, with each sample repeated in triplicate, according to a standard plate template. Plates were incubated for 30 min at 37° C. to allow cell adhesion, and then unbound cells were gently removed by washing 3× with cell adhesion buffer. Remaining attached cells were detected by addition of 100 µl/well p-nitrophenylphosphate (Sigma) solution (15 mg tablet dissolved in 25 ml 50 mM NaAcetate, pH5; 0.5% Triton-X-100), incubation for 30 min at 37° C., and then addition of 50 µl/well 1N NaOH to stop the enzyme reaction. Plates were read by colorimetric detection at 405 nm wavelength using a Tecan Safire II plate reader. Concentration-response curves were constructed by non-linear regression (best fit) analysis, and $IC_{50}$ values were calculated for each compound. EDTA and antibody control samples were evaluated to confirm integrin, and more specifically αvβ5-dependent cell binding in each assay.

Solid Phase Receptor Assay for αvβ8 Function.

Purified human LAP protein (R&D Systems, Inc) diluted to 0.5 µg/ml in TBS buffer (25 mM Tris 7.4, 137 mM NaCl, 2.7 mM KCl, 1 mM $CaCl_2$, 1 mM $MgCl_2$, 1 mM $MnCl_2$) was added to wells (100 µl/well) of a 96-well half-well transparent microtiter plate (Costar 3690), and incubated overnight at 4° C. Wells were washed 3 times with 150 µl TBS, and 200 µl of blocking buffer (TBS with 1% bovine serum albumin) were added. The plate was incubated for 1 hr at 37° C., and then washed 3× with TBS/0.1% bovine serum albumin. Purified recombinant human biotinylated integrin αvβ8 (R&D Systems) was diluted to 0.1 µg/ml in TBS/0.1% bovine serum albumin. Compounds were diluted into the integrin solution and then 50 µl was added to empty wells of the washed LAP-coated plate, according to a standard template, with each sample repeated in triplicate. After incubation for one hour at room temperature, the plate was washed 3× with 150 µl of TBS/0.1% BSA. 50 µl of streptavidin-conjugated horseradish peroxidase (R&D Systems) was added to the wells, and the plate incubated for 20 min at room temperature. The plate was washed 3× with TBS/0.1% bovine serum albumin, 50 µl of TMB substrate (R&D Systems) were added to each well, and the plate was incubated for 20 min at room temperature. The reaction was stopped with 25 µl of Stop Solution (Sigma S5689). Plates were read by colorimetric detection at 650 nm wavelength using a Tecan Safire II plate reader. Concentration-response curves were constructed by non-linear regression (best fit) analysis, and $IC_{50}$ values were calculated for each compound.

Solid Phase Receptor Assay for αvβ1 Function.

Purified human fibronectin (R&D Systems, Inc) diluted to 5 µg/ml in TBS buffer (25 mM Tris 7.4, 137 mM NaCl, 2.7 mM KCl, 1 mM $CaCl_2$, 1 mM $MgCl_2$, 1 mM $MnCl_2$) was added to wells (50 µl/well) of a 96-well half-well transparent microtiter plate (Costar 3690), and incubated overnight at 4° C. Wells were washed 3 times with 150 µl TBS, and 150 µl of blocking buffer (TBS with 1% bovine serum albumin) were added. The plate was incubated for 1 hr at 37° C., and then washed 3× with TBS buffer. Purified recombinant human integrin αvβ1 (R&D Systems 6579-AV) was diluted to 2.0 µg/ml in TBS/0.1% bovine serum albumin. Compounds were diluted into the integrin solution and then 50 µl was added to empty wells of the washed fibronectin-coated plate, according to a standard template, with each sample repeated in triplicate. After incubation for one hour at room temperature, the plate was washed 3× with 150 µl of TBS buffer. To each well, 50 µl of 1 µg/ml biotinylated anti-alpha v antibody (R&D Systems) in TBS/0.1% BSA was added, and the plate was covered and incubated for 1 hr at room temperature. After washing the plate 3× with 150 µl of TBS buffer, 50 µl of streptavidin-conjugated horseradish peroxidase (R&D Systems) was added to the wells, and the plate incubated for 20 min at room temperature. The plate was washed 3× with TBS buffer, 50 µl of TMB substrate (R&D Systems) were added to each well, and the plate was incubated for 20 min at room temperature. The reaction was stopped with 25 µl of Stop Solution (Sigma S5689). Plates were read by colorimetric detection at 650 nm wavelength using a Tecan Safire II plate reader. Concentration-response curves were constructed by non-linear regression (best fit) analysis, and $IC_{50}$ values were calculated for each compound.

Integrin-Mediated TGFβ Activation Assay.

Mink lung epithelial cells stably transfected with a luciferase reporter driven by a portion of the TGFβ-responsive Plasminogen Activator Inhibitor promoter (MLEC-PAI/L) were seeded at a density of 25,000/well in a white-walled, clear-bottom 96-well culture plate (Costar 3610) in 100 µL of assay medium (phenol red-free DMEM+10% fetal bovine serum). The cells were incubated for one hour in ambient air at room temperature, then at 37° C. for three hours in 5% $CO_2$ to allow cell attachment. The medium was aspirated from the wells and 50 µL of compound diluted to 2× in assay medium was applied to each well, followed by 50 µL of assay medium containing 25,000 SW480-β6 cells, a cell line which stably overexpresses recombinant human integrin αvβ6. An untreated MLEC-PAI/L cell group was also included on the plate for a baseline luciferase activity measurement, as well as a no-cell group for a substrate blank. Following overnight co-culture incubation under standard conditions, the assay medium was aspirated from the wells, and a foil seal was applied to the bottom of the plate to prevent cross-detection of luminescence between the sample wells. The assay medium was replaced with 50 μL/well of room-temperature Glo Lysis buffer (Promega E266A). The cells were incubated for five minutes to allow lysis to occur. Fifty microliters of Bright-Glo Luciferase Assay Reagent was then added to each well, and pipetted 4-6 times to thoroughly mix. The assay plate was then read immediately on a luminometer. Data was analyzed by first subtracting the mean substrate blank value from all samples, then dividing by the mean value of the MLEC-PAI/L baseline group to yield a "relative luciferase activity" value (RLA). The RLA values were imported into GraphPad Prism. There the data was transformed as the Log of the compound concentration, and a non-linear fit for a sigmoidal dose-response (variable slope) was used to generate $IC_{50}$ values.

TABLE 2

Biological Assay Results

| Example | α5β1 $IC_{50}$ (nM) | αvβ1 $IC_{50}$ (nM) | αvβ3 $IC_{50}$ (nM) | αvβ5 $IC_{50}$ (nM) | αvβ6 $IC_{50}$ (nM) | αvβ8 $IC_{50}$ (nM) | TGFβ Activation $IC_{50}$ (nM) |
|---|---|---|---|---|---|---|---|
| 1 | 4.2 | 2.5 | 0.8 | 51.7 | 1.5 | 0.23 | 564.3 |

All of the compounds, compositions and methods disclosed and claimed herein can be made and executed without undue experimentation in light of the present disclosure. While the disclosure may have been described in terms of preferred embodiments, it will be apparent to those of skill in the art that variations may be applied to the compounds, compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 5,840,961
U.S. Pat. No. 6,013,651
U.S. Pat. No. 6,028,223
U.S. Pat. No. 6,414,180
Adachi et al., Clin. Cancer Res., 6(1):96-101, 2000.
Asano et al., J. Immunol., 175(11):7708-7718, 2005.
Austr. J. Chem., 34(6):1319-1324, 1981.
Avraamides et al., Nat. Rev. Cancer, 8(8):604-617, 2008.
Awasthi et al., J. Org. Chem., 70:5387-5397, 2005.
Bax et al., J. Biol. Chem., 278(36):34605-34616, 2003.
Becker et al., Tetrahedron, 39:4189-4192, 1983.
Bhaskar et al., J. Transl. Med., 5:61, 2007.
Blase et al., Int. J. Cancer, 60(6):860-866, 1995.
Collo, J. Cell Sci., 112 (Pt 4):569-578, 1999.
Danen et al., Histopathology, 24(3):249-256, 1994.
Edward, Curr. Opin. Oncol., 7(2):185-191, 1995.
Engleman et al., J. Clin. Invest., 99(9):2284-2292, 1997.
Faulconbridge et al., Tetrahedron Lett., 41:2679-2681, 2000.
Ferrari et al., Proc. Natl. Acad. Sci. USA, 103(46):17260-17265, 2006.
Gao and Brigstock, Gut, 55:856-862, 2006.
Girsch et al., J. Med. Chem., 50:1658-1667, 2007.
Girsch et al., J. Med. Chem., 51:6752-6760, 2008.
Greene & Wuts, Protective Groups in Organic Synthesis, 3$^{rd}$ Ed., John Wiley, 1999.
Handbook of Pharmaceutical Salts: Properties, and Use, Stahl and Wermuth (Eds.), Verlag Helvetica Chimica Acta, 2002.
Horan et al., Am. J. Respir. Crit. Care Med., 177(1):56-65, 2008.
Kim et al., Am. J. Pathol., 156(4):1345-1362, 2000.
Kurahashi et al., J. Am. Chem. Soc., 133(21):8307-8316, 2011.
Landis et al., Organic Process Research & Development, 6:539-546, 2002.
Li et al., Invest. Ophthalmol. Vis. Sci., 50(12):5988-5996, 2009.
Livant et al., J. Clin. Invest., 105(11):1537-1545, 2000.
Lobert et al., Dev. Cell, 19(1):148-159, 2010.
March's Advanced Organic Chemistry: Reactions, Mechanisms, and Structure, 2007.
Melton et al., J. Clin. Invest., 120(12):4436-4444, 2010.
Millard et al., Theranostics, 1:154-88, 2011.
Mu et al., Cell Biol., 157(3):493-507, 2002.
Munger et al., Cell., 96(3):319-328, 1999.
Munger et al., Mol. Biol. Cell, 9:2627-2638, 1998.
Nandrot et al., Am. J. Physiol. Cell Physiol., 290 (4):C1256-1262, 2006.
Nishimura, Am. J. Pathol., 175(4):1362-1370, 2009.
Nomura et al., Chemistry—A Europ. J., 13(16):4433-4451, 2007.
Organic Process Research & Development, 8:51-61, 2004.
Organic Process Research & Development, 8:571-575, 2004.
Perdih, Curr. Med. Chem., 17(22):2371-2392, 2010.
Popov et al., J. Hepatol., 48(3):453-464, 2008.
Rico, Tett. Let., 35:6599-6602, 1994.
Scotton et al., J. Clin. Invest., 119(9):2550-2563, 2009.
Suchiro et al., J. Biochem., 128(4):705-710, 2000.
Vogel's Textbook of Practical Organic Chemistry, 5$^{th}$ Ed., p:1040, 1989.
Wipff et al., J. Cell Biol., 179(6):1311-1323, 2007.
Yang et al., Development, 119(4):1093-1105, 1993.
Yoshimura, Curr. Top. Microbiol. Immunol., 350:127-147, 2011.
Zahn et al., Arch. Ophthalmol., 127(10):1329-1335, 2009.
Zahn et al., Invest. Ophthalmol. Vis. Sci., 51(2):1028-1035, 2010

What is claimed:
1. A compound of the formula:

(I)

wherein X is bromo or iodo,
or a pharmaceutically acceptable salt or tautomer thereof.

2. The compound of claim 1, further defined as:
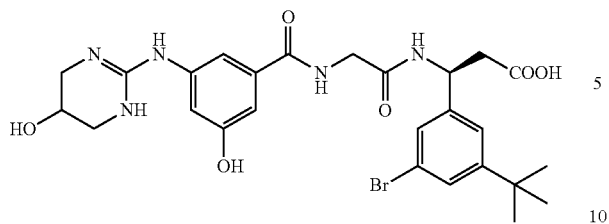
or a pharmaceutically acceptable salt or tautomer thereof.
3. The compound of claim 1, further defined as:
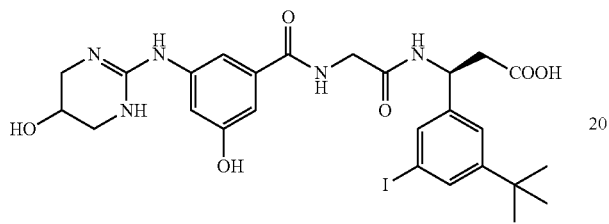
or a pharmaceutically acceptable salt or tautomer thereof.
4. A pharmaceutical composition comprising:
a) the compound of claim 1; and
b) an excipient.
* * * * *

UNITED STATES PATENT AND TRADEMARK OFFICE
CERTIFICATE OF CORRECTION

PATENT NO.        : 8,716,226 B2
APPLICATION NO.   : 13/944319
DATED             : May 6, 2014
INVENTOR(S)       : Peter Ruminski and David Griggs Page 1 of 1

It is certified that error appears in the above-identified patent and that said Letters Patent is hereby corrected as shown below:

On the title page, item (56) References Cited - Other Publications, delete the 7th reference on page 2 "Clark, et al., "Pilot-Plant Preparation of an αv133 Integrin Antagonist. Part 2. Synthesis of N-[2-(5-Hydroxy-4,6-tetrahydropyrimidine)]-3-amino-5-hydroxybenzoic Acid," *Organic Process Research & Development*, 8:571-575, 2004." and insert --Clark, et al., "Pilot-Plant Preparation of an αvβ3 Integrin Antagonist. Part 2. Synthesis of N-[2-(5-Hydroxy-4,6-tetrahydropyrimidine)]-3-amino-5-hydroxybenzoic Acid," *Organic Process Research & Development*, 8:571-575, 2004.-- therefor.

On the title page, item (56) References Cited - Other Publications, delete the 22nd reference on page 3 "Yoshimura and Muto, "TGF-βfunction in immune suppression," *Curr Top Microbiol Immunol.*, 350:127-147, 2011." and insert --Yoshimura and Muto, "TGF-β function in immune suppression," *Curr Top Microbiol Immunol.*, 350:127-147, 2011.-- therefor.

Signed and Sealed this
Fifth Day of August, 2014

Michelle K. Lee
*Deputy Director of the United States Patent and Trademark Office*